(12) United States Patent
Gatt et al.

(10) Patent No.: US 9,579,212 B2
(45) Date of Patent: *Feb. 28, 2017

(54) TISSUE ENGINEERED FIBROCARTILAGE REPLACEMENT

(71) Applicant: Rutgers, The State University of New Jersey, New Brunswick, NJ (US)

(72) Inventors: Charles J. Gatt, Skillman, NJ (US); Eric A. Balint, East Brunswick, NJ (US); Michael G. Dunn, Manalapan, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 113 days.

This patent is subject to a terminal disclaimer.

(21) Appl. No.: 14/145,347

(22) Filed: Dec. 31, 2013

(65) Prior Publication Data

US 2014/0180420 A1    Jun. 26, 2014

Related U.S. Application Data

(63) Continuation of application No. 12/995,930, filed as application No. PCT/US2009/045985 on Jun. 2, 2009, now Pat. No. 8,623,085.

(Continued)

(51) Int. Cl.
*A61F 2/08* (2006.01)
*A61F 2/44* (2006.01)
(Continued)

(52) U.S. Cl.
CPC ............ *A61F 2/442* (2013.01); *A61F 2/3094* (2013.01); *A61F 2/30756* (2013.01);
(Continued)

(58) Field of Classification Search
CPC ................ A61F 2/3872; A61F 2/30756; A61F 2002/30757; A61F 2002/30761;
(Continued)

(56) References Cited

U.S. PATENT DOCUMENTS 3,867,728 A * 2/1975 Stubstad ................. A61F 2/441
128/DIG. 21
5,158,574 A  10/1992 Stone
(Continued)

FOREIGN PATENT DOCUMENTS

EP      0372811 A1    6/1990
FI    CA 2290787 A1 * 12/1998    ......... A61F 2/30721
(Continued)

*Primary Examiner* — Andrew Iwamaye
(74) *Attorney, Agent, or Firm* — Fox Rothschild LLP

(57) ABSTRACT

Fibrocartilage implants characterized by circumferential fiber networks embedded in arcuate or torroidal scaffolds with orthogonal fiber networks embedded therein to prevent separation of the circumferential fiber networks. The fiber networks convert axial compressive forces on the scaffolds to tensile loads on the circumferential fibers. Artificial knee meniscus and vertebral disc implants are disclosed, as well as articular disc implants for joints such as the temporomandibular joint and wrist. Methods for implanting the fibrocartilage devices are also disclosed.

17 Claims, 21 Drawing Sheets

Related U.S. Application Data

(60) Provisional application No. 61/130,791, filed on Jun. 2, 2008.

(51) Int. Cl.
  | | | |
  |---|---|---|
  | *A61F 2/42* | (2006.01) | |
  | *A61F 2/38* | (2006.01) | |
  | *A61F 2/30* | (2006.01) | |

(52) U.S. Cl.
  CPC .......... *A61F 2/3872* (2013.01); *A61F 2/4261* (2013.01); *A61F 2/44* (2013.01); *A61F 2002/30757* (2013.01); *A61F 2002/30761* (2013.01); *A61F 2002/30762* (2013.01); *A61F 2002/30766* (2013.01); *A61F 2002/4435* (2013.01); *A61F 2002/4445* (2013.01); *A61F 2002/4495* (2013.01); *A61F 2310/00371* (2013.01); *A61F 2310/00383* (2013.01); *A61F 2310/00982* (2013.01); *A61F 2310/00994* (2013.01); *Y10T 156/10* (2015.01)

(58) Field of Classification Search
  CPC .. A61F 2002/30762; A61F 2002/30766; A61F 2/44; A61F 2/442; A61F 2/3094; A61F 2/4261; A61F 2002/4435; A61F 2002/4445; A61F 2002/4495

See application file for complete search history.

(56) References Cited

U.S. PATENT DOCUMENTS

| | | | |
|---|---|---|---|
| 9,078,756 B2* | 7/2015 | Gatt et al. | |
| 2002/0022884 A1 | 2/2002 | Mansmann | |
| 2004/0133275 A1 | 7/2004 | Mansmann | |
| 2005/0027364 A1* | 2/2005 | Kim | A61F 2/4425 623/17.13 |
| 2005/0055099 A1* | 3/2005 | Ku | A61F 2/442 623/17.16 |
| 2005/0177249 A1 | 8/2005 | Kladakis et al. | |
| 2005/0234549 A1* | 10/2005 | Kladakis et al. | 623/14.12 |
| 2007/0150063 A1* | 6/2007 | Ruberte | A61F 2/442 623/17.16 |
| 2008/0228273 A1* | 9/2008 | McLeod | A61F 2/442 623/17.11 |

FOREIGN PATENT DOCUMENTS

| | | |
|---|---|---|
| JP | 2003-210499 A | 7/2003 |
| WO | 2006/064025 A2 | 6/2006 |

* cited by examiner

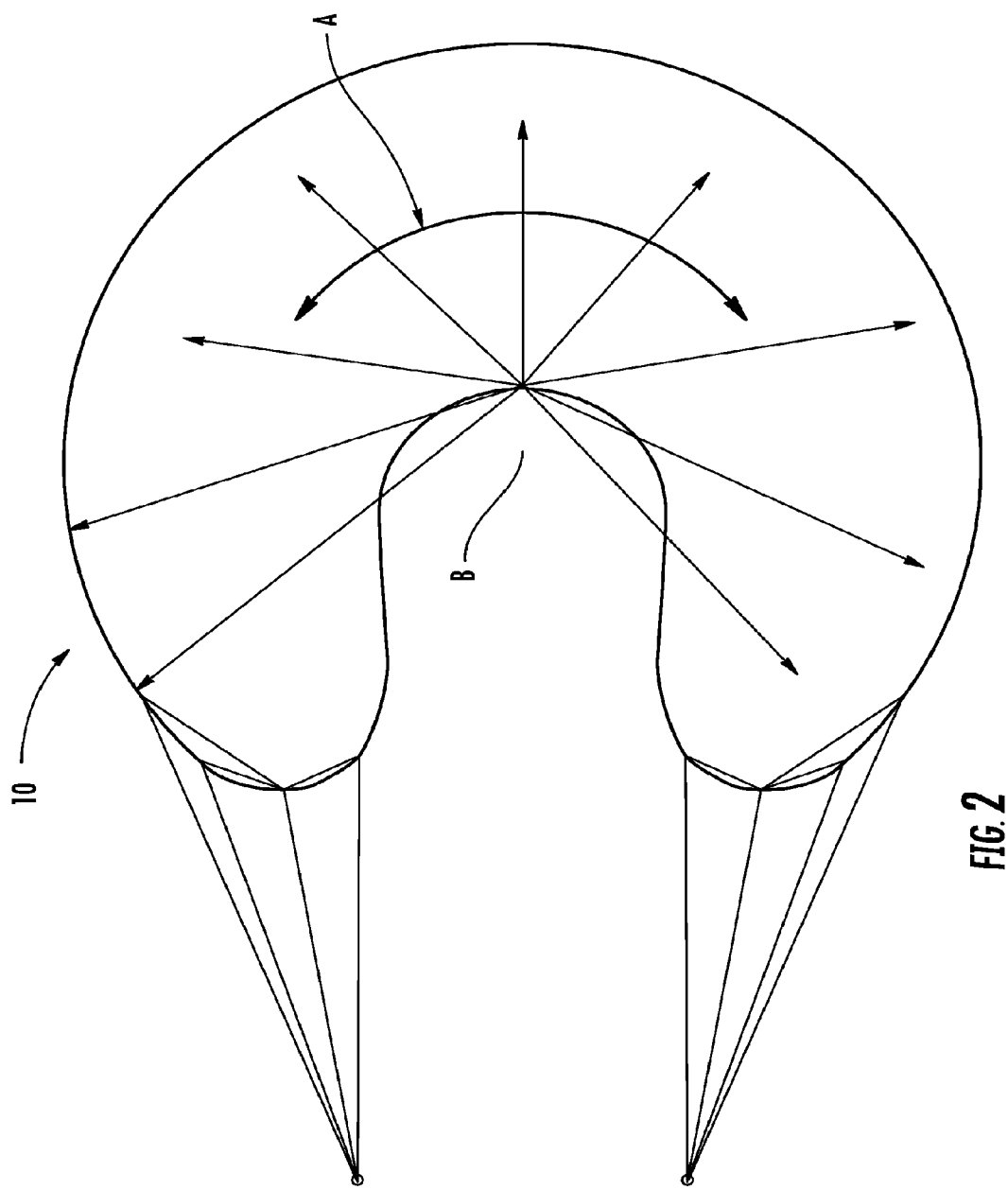

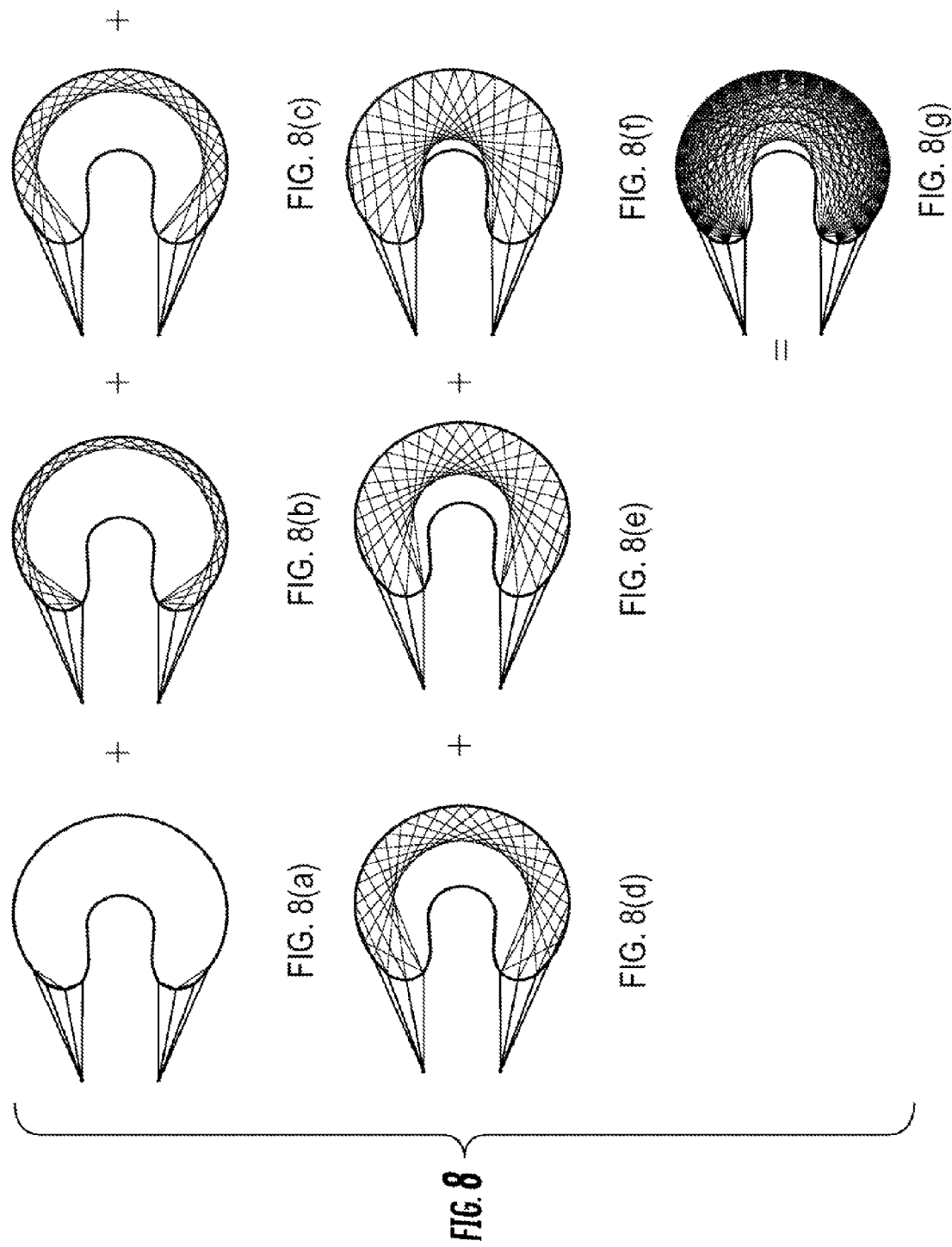

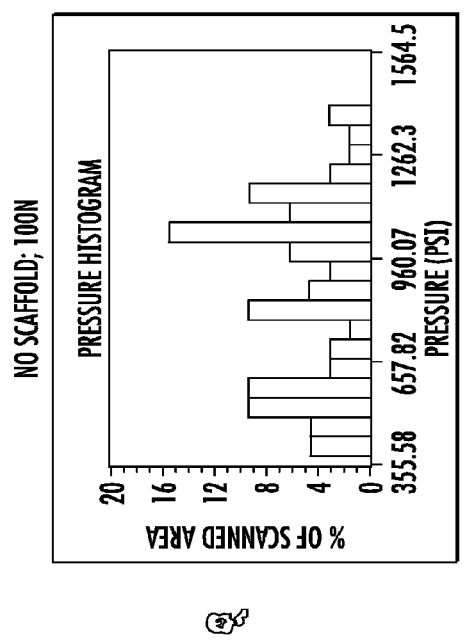
FIG. 10A
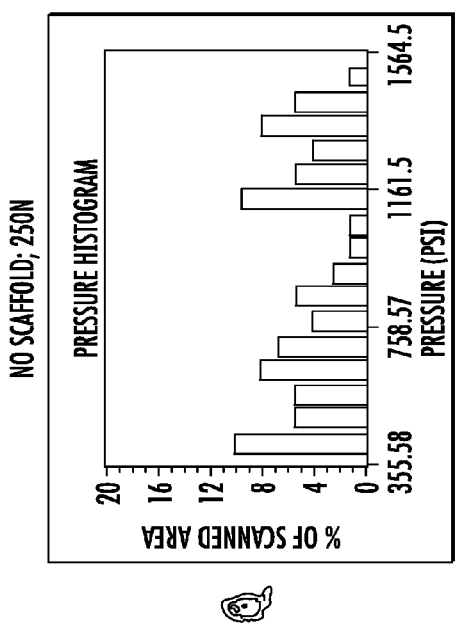
FIG. 10B
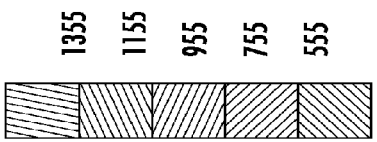
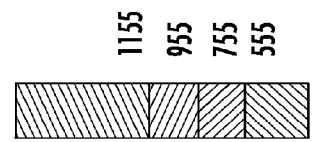

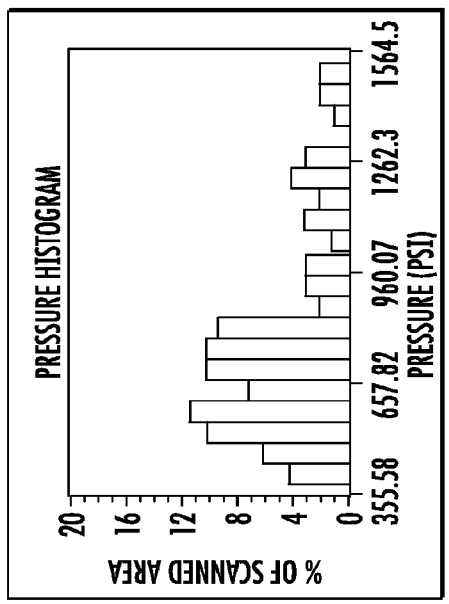
FIG. 11A
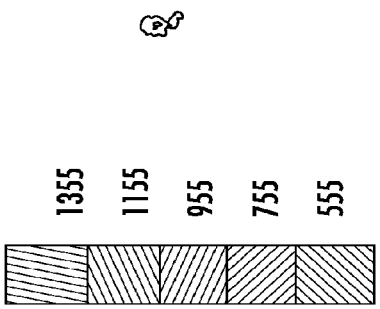
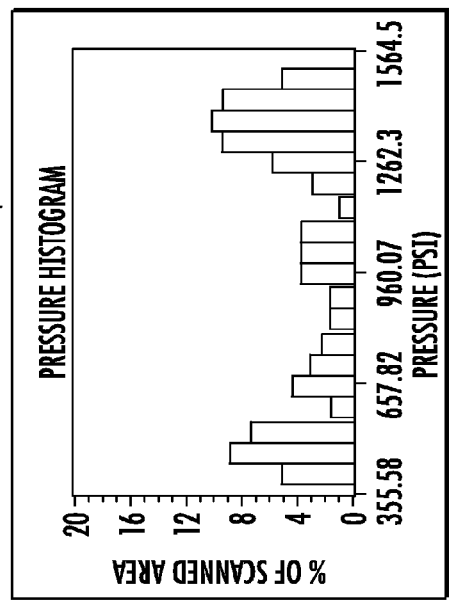
FIG. 11B
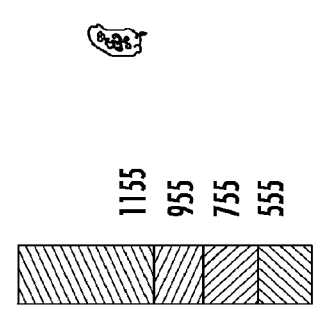

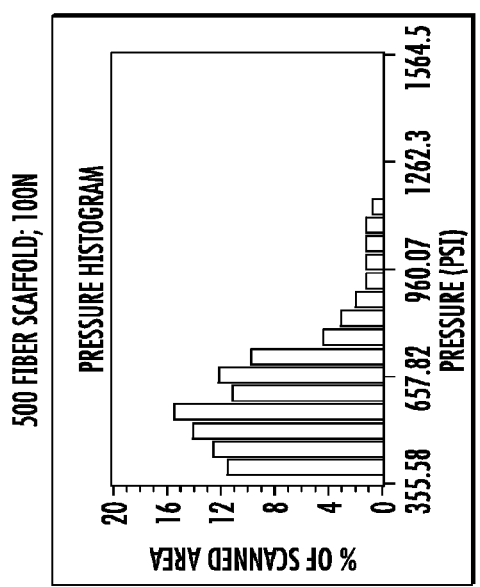
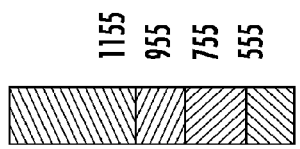
FIG. 12A
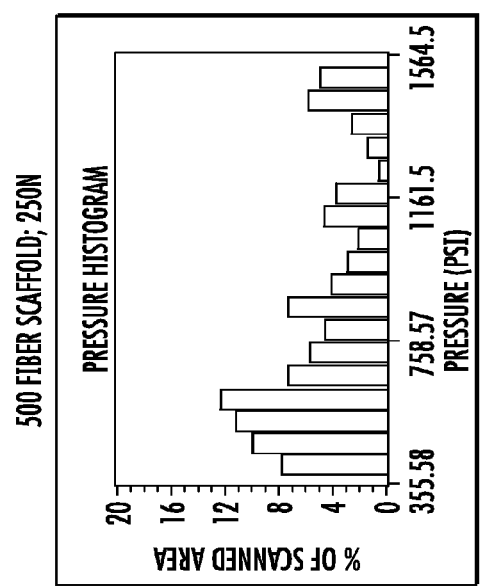
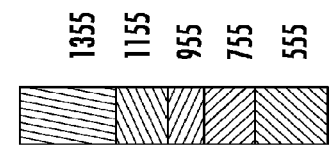
FIG. 12B

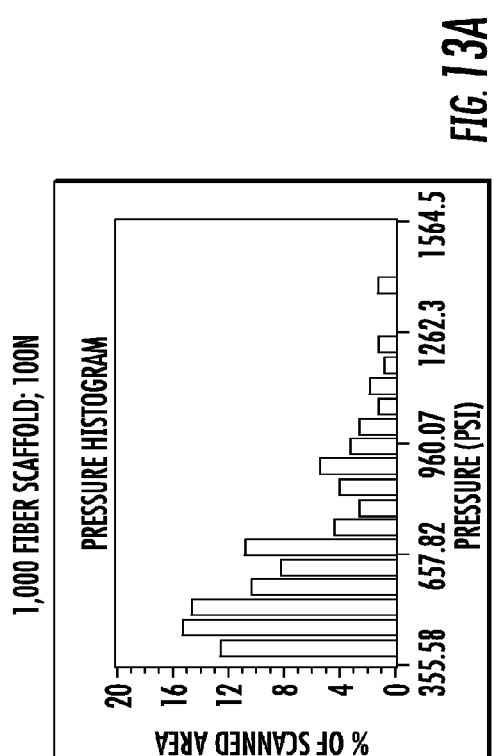
FIG. 13A
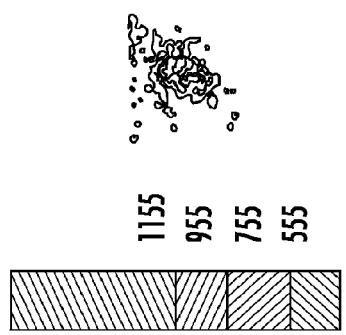
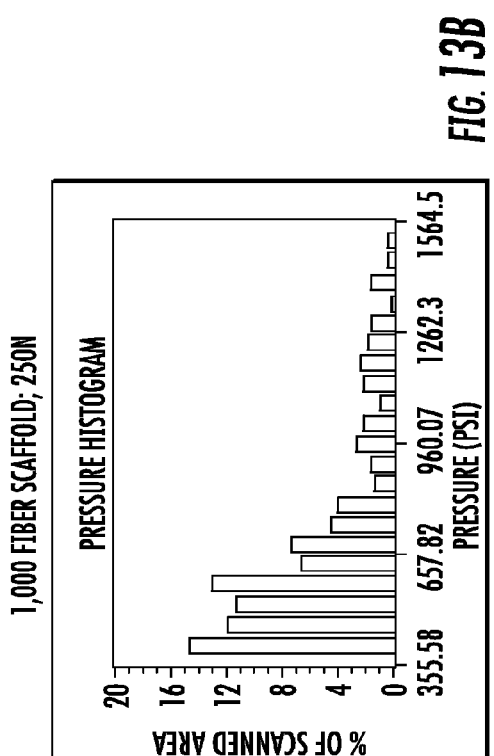
FIG. 13B
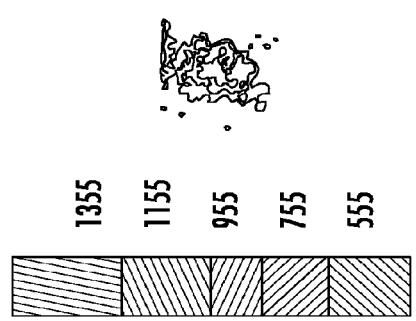

TISSUE ENGINEERED FIBROCARTILAGE REPLACEMENT

CROSS-REFERENCE TO RELATED APPLICATIONS

This application is a continuation of U.S. application Ser. No. 12/995,930 which is the 35 U.S.C. §371 National Phase Application of International Application Serial No. PCT/US09/45985 filed Jun. 2, 2009, now U.S. Pat. No. 8,623,085, which claims the benefit under 35 U.S.C. §119(e) of U.S. Provisional Application Ser. No. 61/130,791, filed Jun. 2, 2008, the disclosures of which are incorporated by reference in their entireties.

FIELD OF THE INVENTION

This invention relates to methods and devices for replacement of severely damaged fibrocartilage tissue and, in particular, to the replacement of the lateral or medial meniscus of the knee.

BACKGROUND

The menisci are two C-shaped discs of fibrocartilage found between the condyles of the femur and the tibial plateau which play a critical role in the load transmission, load distribution, shock absorption, joint stability, and lubrication of the knee. Despite the recognized importance of the tissue, arthroscopic removal of a torn meniscus is one of the most common orthopedic procedures performed in the United States. Because the tissue has limited healing potential, the clinical outcomes of subtotal meniscectomies are generally poor. At this time, a reliable surgical procedure to replace significant loss of meniscal tissue does not exist. There is no autologous procedure to replace the meniscus and the results of allograft replacement are unreliable.

Another approach is that of tissue engineering. Current approaches include synthetic polymer scaffolds and collagen meniscus implants. With synthetic polymer scaffolds, polyurethane sponges are used to replace the meniscus. This approach has led to inconsistent results. Fibrocartilage growth is seen in some studies using this technology while in others fibrous tissue did not remodel into fibrocartilage. The underlying cartilage was protected in some studies but not protected in others.

Another type of meniscus implant uses a sponge containing collagen, hyaluronic acid and chondroitin sulfate. There is promising preliminary data for this implant, but it is not widely accepted by the orthopedic community because of issues with cytotoxic byproducts of cross-linking and scaffold shrinkage.

Both of these approaches generate an amorphous structure, the mechanical properties of which may not be appropriate for a device designed to replace the meniscus. Thus, while scaffold technology holds promise, no methods have met with the clinical success necessary for acceptance by the orthopedic community. There remains a need for a tissue engineered scaffold with the necessary mechanical properties and biocompatibility for treatment of significant meniscal damage.

SUMMARY

This need is met by the present invention. The present invention incorporates the discovery that the shortcomings of prior art implants can be overcome by reinforcement of the scaffold with a fiber matrix extending in a circumferential direction along the scaffold, the fibers of which are in turn held together by scaffold matrix fibers embedded orthogonally to the circumferential fibers. The resulting configuration behaves like natural fibrocartilage that translates an axial compressive load into a circumferential tensile load. When the implant is an artificial knee meniscus, the implant translates the axial compressive load exerted by the femur on the implant into a tensile load propagated in the circumferential direction of the scaffold, like a natural meniscus.

In one aspect, the present invention thus provides a fiber reinforced implant for use as a temporary replacement for significantly damaged fibrocartilage tissue, such as meniscal tissue of the knee, jaw or wrist, or an intervertebral disc. The inventive implant is constructed of resorbable natural or synthetic biomaterials which allow for infiltration, attachment and proliferation of cells from the surrounding tissues. The implant of the present invention is a natural or synthetic scaffold having the shape and geometry of the original undamaged fibrocartilage with a reinforcing matrix embedded therein.

Therefore, according to one embodiment of the present invention, an artificial fibrocartilage implant is provided in which an arcuate or torroidal scaffold has a circumferential fiber network embedded therein and an orthogonal fiber network embedded in the scaffold to prevent separation of the circumferential fiber network, wherein the fiber networks convert an axial compressive force on the scaffold to tensile loads along the circumferential fiber network.

According to arcuate embodiments of the present invention, the arcuate scaffold has an anterior end, a posterior end and a middle section therebetween defining a curved path between the anterior and posterior ends. The circumferential fiber network extends between the anterior and posterior ends along the path of the curve and exits the anterior and posterior ends of the scaffold to form respective anterior and posterior attachment points.

According to a more specific arcuate embodiment of the present invention, the arcuate implant is fabricated in the shape of a knee meniscus. Another embodiment of this aspect of the present invention therefore provides an artificial knee meniscus implant with a c-shaped scaffold having an arcuate middle section extending between an anterior end and a posterior end and a reinforcing fiber network embedded in the scaffold, wherein the fibers of the network exit each end of the scaffold to form respective anterior and posterior attachment points and the fiber network converts an axial compressive force on the scaffold to tensile loads on the attachment points.

According to a more specific embodiment of the knee meniscus of the present invention, at least a portion the fiber network extends along the arcuate middle section in a substantially circumferential direction. According to an even more specific embodiment, the fiber network further includes an orthogonal fiber network embedded within the scaffold to prevent separation of the circumferential fiber network. In a preferred embodiment the artificial knee meniscus has a wedge-shaped cross-section substantially equivalent to a human knee meniscus.

According to another more specific embodiment of the arcuate and torroidal menisci of the present invention, the inventive implants have at least one peripheral attachment point. In a preferred embodiment, at least one peripheral attachment point coincides with a point at which the circumferential fiber network intersects with the orthogonal fiber network. In another preferred embodiment, the fiber network(s) extend throughout the wedge-shaped cross section of the arcuate middle section.

According to one torroidal embodiment of the invention, the inventive implant is a torroidal-shaped scaffold having the circumferential and orthogonal fiber networks of the present invention. Such a device is particularly useful for replacement of intervertebral discs or temporomandibular joint discs. Artificial implants according to this embodiment of the present invention are fabricated in the shape of a vertebral disc or an articular disc for a joint.

More specific torroidal embodiments have at least one peripheral attachment point. In preferred versions of this embodiment, at least one peripheral attachment point coincides with a point at which the circumferential fiber network intersects with the orthogonal fiber network.

According to one torroidal embodiment torroidal implants are fabricated in the shape of a vertebral disc, wherein the torroidal-shaped scaffold defines an interior cavity filled with a biocompatible material with physical properties equivalent to the properties of the nucleus pulposus of a human vertebral disc. According to another torroidal embodiment, torroidal implants are fabricated in the shape of articular disc, for example, in the shape of the meniscus of the temporomandibular joint or the wrist.

In any of the inventive embodiments at least one of the scaffold, the circumferential fiber network or the orthogonal fiber network may be formed from a material selected from proteins, proteoglycans, biocompatible synthetic polymers and combinations thereof. In some embodiments the material is bioresorbable. In other embodiments the proteins comprise collagen, and in certain of these embodiments the collagen is cross-linked.

In any of the inventive embodiments at least one of the scaffold, the circumferential fiber network or orthogonal fiber network is formed from a biocompatible synthetic polymeric material. In some embodiments the polymeric material is bioresorbable.

According to another aspect of the present invention, a method is provided for replacement of a damaged knee meniscus. Methods according to this aspect of the present invention include the steps of:

replacing a damaged meniscus with a knee meniscus implant according to the present invention by inserting a knee meniscus implant according to the present invention, having anterior and posterior attachment points, between the tibial plateau characterized by having anterior and posterior anchor plugs inserted therein, and the corresponding femur condyle; and securing the anterior and posterior attachment points of the implant to the corresponding anterior and posterior anchor plugs.

According to yet another aspect of the present invention, a method is provided for fabricating a soft tissue repair implant such as a meniscus implant. Methods according to this aspect of the present invention include the steps of:

forming a reinforcement matrix with at least one fiber; and embedding the reinforcement matrix into a scaffold, wherein the scaffold has an arcuate middle section extending between an anterior end and a posterior end; and wherein the at least one fiber exits each end of the scaffold.

By creating an implant that has the same geometry as that of the normal tissue, along with a network of embedded, reinforcing fibers, the mechanics of the natural tissue can be replicated. As cells infiltrate this implant, they will experience the same mechanical environment of that of a normal tissue, thus promoting the formation of neofibrocartilaginous tissue which has the biological and mechanical properties to function as a load-bearing structure.

BRIEF DESCRIPTION OF THE FIGURES

FIGS. 1 and 2 are top views of one embodiment of the instant device;

FIGS. 8(a)-8(g) show the organization of embedded fibers;

FIGS. 10A-10B present the results of an advanced mechanical evaluation for the "No Scaffold" group;

FIGS. 11A-11B present the results of an advanced mechanical evaluation for the "100% Collagen Scaffold" group;

FIGS. 12A-12B present the results of an advanced mechanical evaluation for the "500 Fiber Scaffold" group;

FIGS. 13A-13B present the results of an advanced mechanical evaluation for the "1000 Fiber Scaffold" group;

DETAILED DESCRIPTION

The instant implant improves upon current meniscus scaffolding approaches in conjunction with current tendon/ligament scaffolding approaches. With regard to tissue-type, the meniscus can be viewed as a combination of organized fibrous connective tissue predominant at its outer portion (i.e. tendon/ligament) and cartilaginous tissue at its inner portion. This extracellular matrix (ECM) organization occurs because of the way the meniscus is loaded under normal conditions.

For the meniscus of the knee, during static or dynamic weight-bearing the tissue is compressed by the femur. Because of the geometry of the meniscus (C-shaped with wedge-shaped cross-section), this axial load extrudes the tissue from the joint capsule. This extrusion is resisted by the anterior and posterior attachments to the tibial plateau, resulting in the generation of tensile hoop stresses directed along the circumferentially arranged collagen fibers within the tissue.

The hoop stresses are predominantly developed near the periphery of the tissue, where the ECM is more tendon-like. Near the inner margin, the tissue primarily undergoes standard compression, meaning the ECM organization is closer to that of cartilage.

Although the instant implant is described in relation to making and using a knee meniscus replacement device, the teachings of the instant disclosure may also be applied to make and use implants for replacing other tissues similar in nature and function to the meniscus, such as intervertebral discs, temporomandibular discs, wrist menisci, and the like. These tissues are similar to the knee meniscus in that they are composed of fibrocartilage and function as load transmitters and distributors to prevent high-stress bone-on-bone contact that is detrimental to the underlying cartilage. It will also be understood that the instant teachings may be applied to make and use implants for both human and animal patients.

Figure 1:
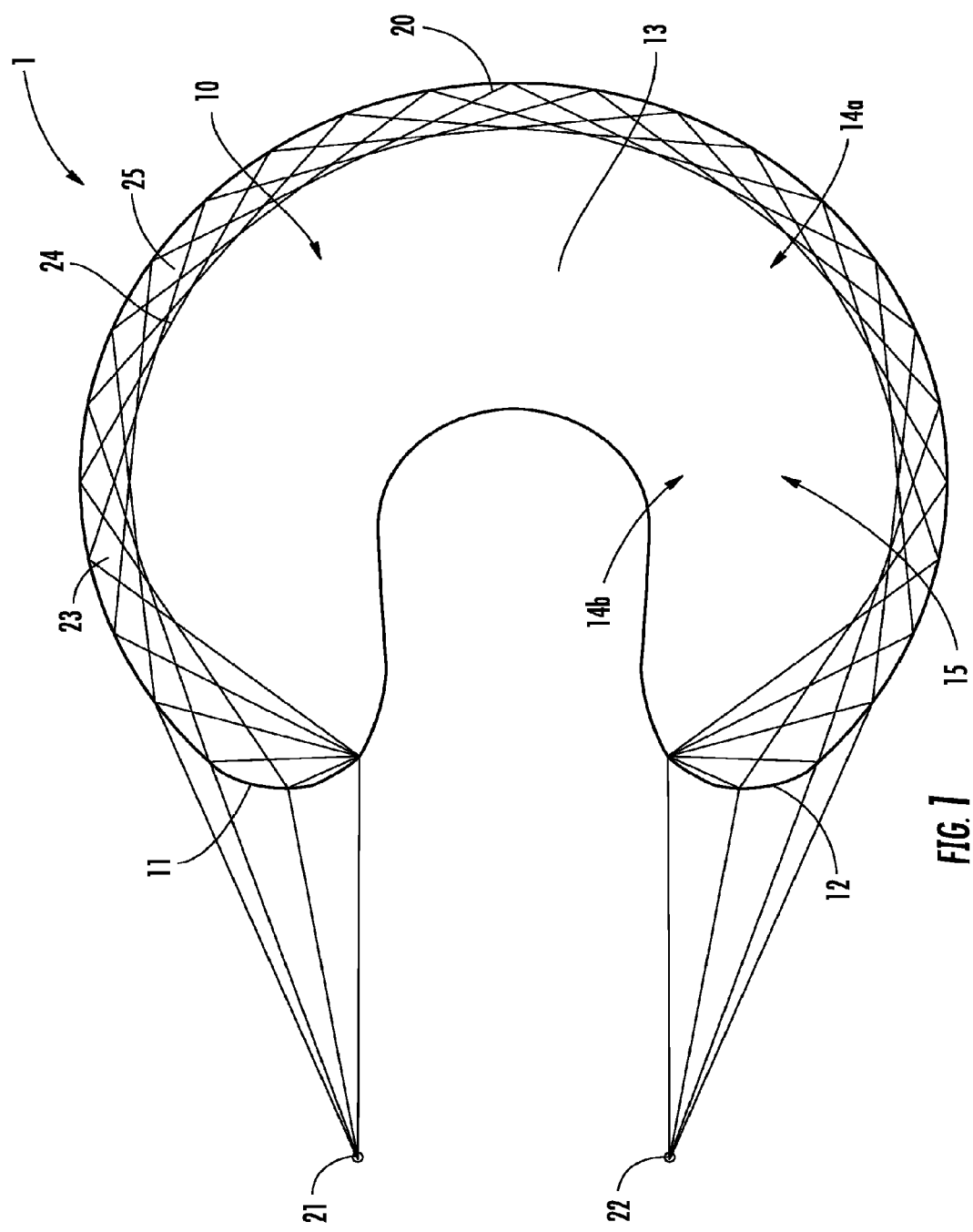

Accordingly, one aspect of the invention provides an implant 1 comprising a scaffold 10 and reinforcing matrix 14 embedded in the scaffold 10 as shown in FIG. 1. The shape and geometry of the scaffold, and consequently the implant, is based on the shape and geometry of the soft tissue in need of replacement. Thus, in the case of a meniscus implant, the scaffold may be constructed as a c-shaped disc with a wedge-like cross-section, similarly to a knee meniscus. Furthermore, it may be shaped concave on the top, which would come in contact with femur, and flat on the bottom, which would rest on the tibial plateau. Although not necessary, the reinforcing matrix may also have the same general shape and geometry as the scaffold.

The scaffold 10 includes an anterior end 11, a posterior end 12 and a middle section 13 defining a path between the anterior end 11 and the posterior end 12. In a meniscus replacement device, the middle section is essentially arc-shaped and defines a curved path between said anterior and posterior ends. The scaffold also has peripheral regions 14a and 14b and an inner region 15 between the peripheral regions 14a and 14b. Referring to FIGS. 1-2, for the purposes of the instant disclosure, the circumferential direction of the scaffold is indicated by arrow A and generally extends along the middle section of the scaffold.

Figure 3A:
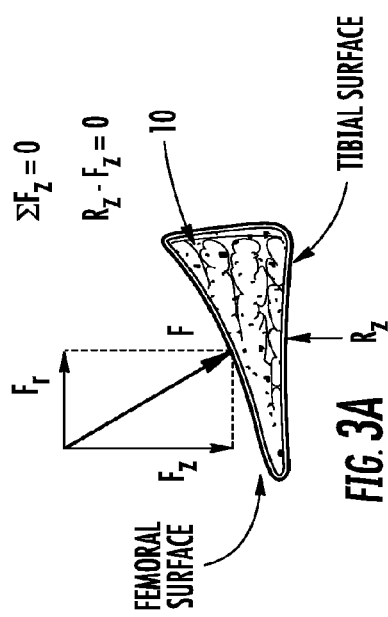
FIGS. 3A-3B present a diagram of forces on the instant device when the device is implanted.
Figure 3B:
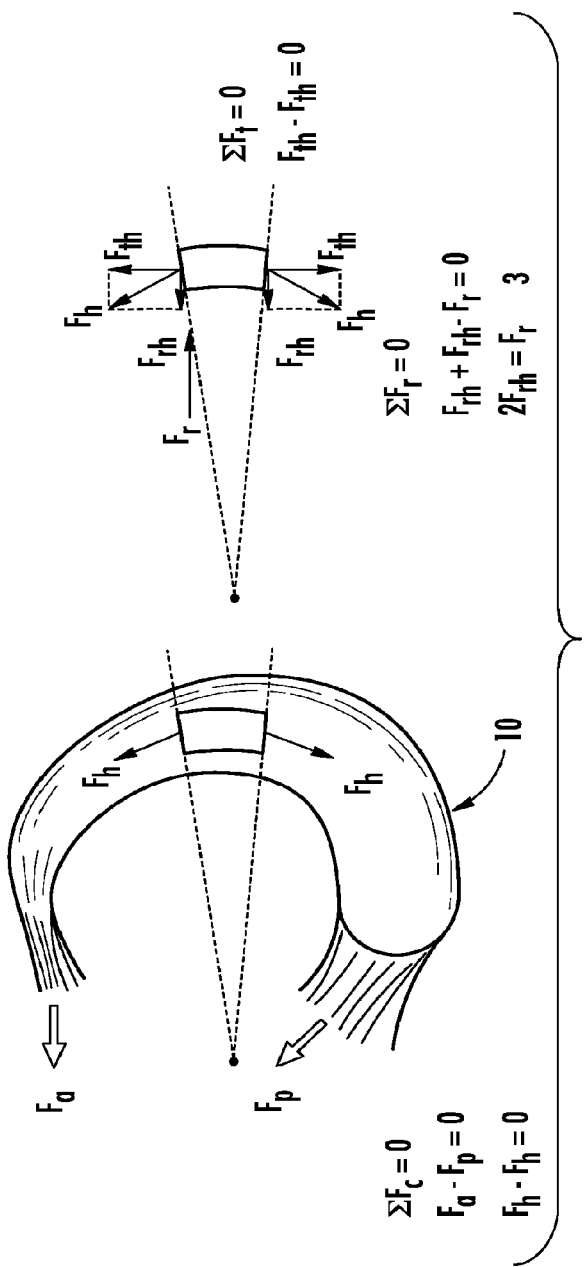

Referring to FIG. 3A, in operation, a compressive force F would normally be applied on the scaffold 10 in axial direction, which is indicated by an arrow F. Referring to FIG. 3B, the design of the implant is such that the compressive force F on the scaffold 10 is translated into tensile hoop stresses in circumferential direction, as shown by arrows $F_h$. For consistency, the same terminology is also applied in reference to the reinforcing matrix and the implant as a whole.

Referring back to FIG. 1, the reinforcing matrix 20 may be formed by at least one fiber 23 extending between the anterior end 11 and posterior end 12 of the scaffold 10 and exiting each end to form an anterior attachment point 21 and a posterior attachment point 22. As used herein, the term "fiber" refers to any generally elongated member consisting of a single component, e.g. monofilament suture, or multiple components, e.g. multifilament suture. The fibers may be formed by any suitable method for forming the biocompatible materials from which they are made into a fiber or filament. The fibers may be drawn, extruded, cast, etc. The physical property of the fiber, such as tensile strength, cross-sectional area, diameter, flexibility, etc., may vary over the length of the fiber. In some embodiments, multiple fibers may be used to form the reinforcing matrix. The fibers may be made of the same or different materials and may follow the same or different paths.

Preferably, at least a portion of the fiber 21 forming the reinforcing matrix 20 is positioned substantially in circumferential direction 24. In some embodiments, the fiber 23 forming the reinforcing matrix 20 may be arranged in two different arrangements: the circumferential arrangement 24 and an orthogonal arrangement 25. As used herein, the terms "orthogonal arrangement," or "arranged orthogonally," include, as one example, an arrangement of fibers extending in directions substantially parallel to arrows B in FIG. 2 at various angles in relation to the scaffold.

Figure 4:
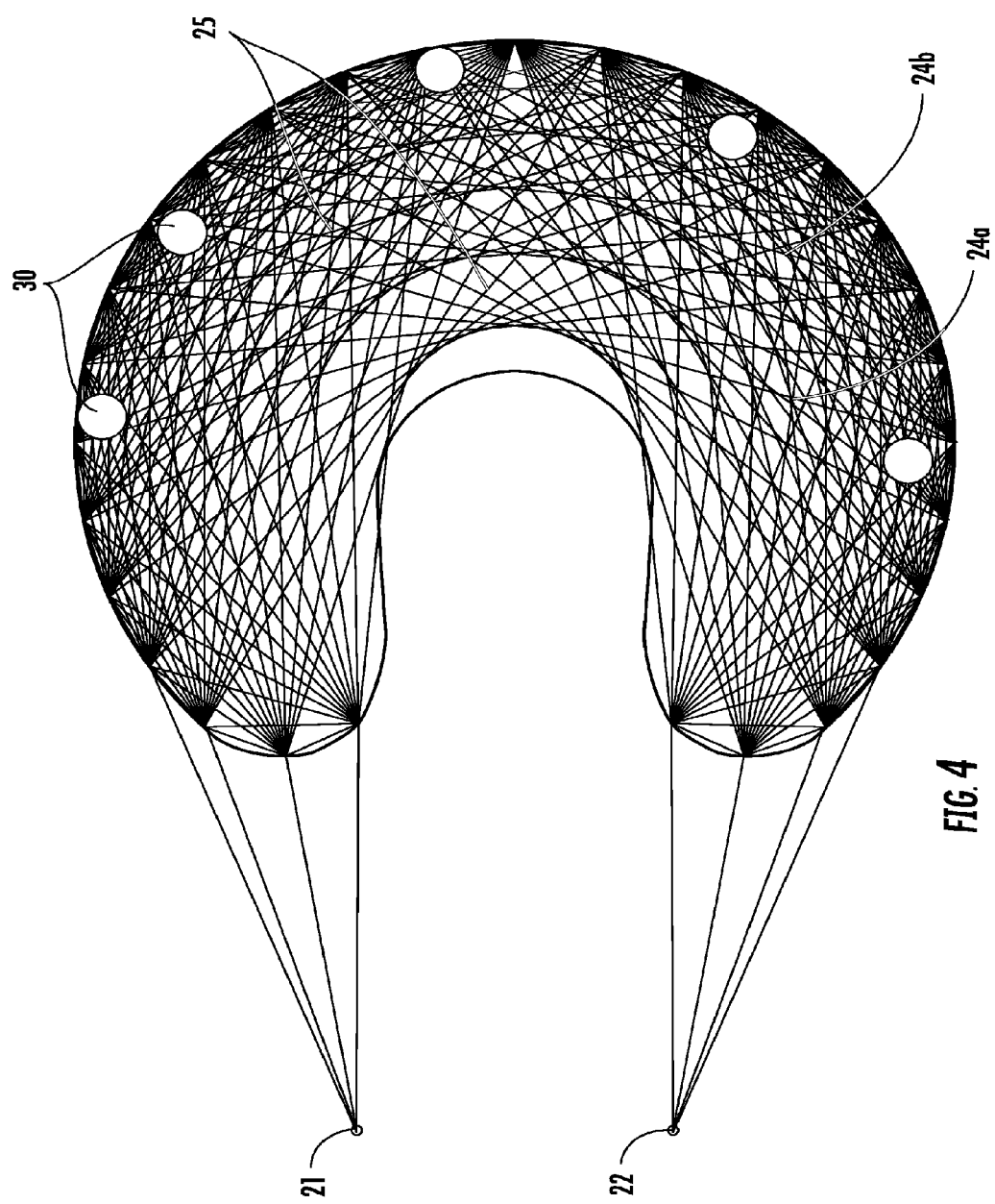
FIG. 4 is a top view of the device in FIGS. 1 and 2 with another embodiment of the reinforcing matrix.

In reference to FIG. 4, the reinforcing matrix 20 comprises one or more circumferential fibers 24 and one or more orthogonal fibers 25. The term "circumferential fiber" refers to fiber that extends between the anterior end and posterior end of the scaffold along the middle section of the scaffold and is positioned at least in part substantially parallel to the circumferential axis. The term "orthogonal fiber" refers to fibers that cross the circumferential fibers at various angles to keep them from separating. Keeping the circumferential fibers from separating increases the durability and longevity of the implant. For convenience, terms "circumferential fiber network" and "orthogonal fiber network" may be used herein to refer to multiple circumferential fibers or multiple orthogonal fibers, respectively.

As noted above, in operation the compressive force on the device in the axial direction is translated into tensile hoop stresses in the circumferential direction. The hoop stresses propagate along the circumferential fibers. In vivo, as meniscal tissue grows into the implant and cells attach to the fiber networks, cells on or about the circumferential fibers experience the same mechanical environment as in a normal meniscus, resulting in the formation of tissue with the essentially the same organization and directionality of collagen fibers as the original meniscus.

The reinforcing matrix may be formed with one single continuous fiber arranged both circumferentially and orthogonally, or, the matrix may be formed using multiple fibers. In such embodiments, the circumferential fibers as well as orthogonal fibers may be formed by the same or different strands of fiber or a combination thereof.

The instant implant includes an anterior attachment point 21 and a posterior attachment point 22 for attaching the implant to tissue adjacent to the implantation site. These attachment points are formed by fiber exiting from the anterior and posterior end of the scaffold, respectively. Referring to FIGS. 3A-3B, attaching the implant in place by these attachment points converts axial compressive force F on the scaffold 10 and reinforcing matrix 20 into tensile loads along the circumferential fibers and on the anterior and posterior attachment points. The forces on the anterior and posterior attachment points are presented as force $F_a$ and force $F_p$, respectively.

Moreover, in some embodiments, the implant may comprise one or more additional attachment points 30 formed in the middle section of the scaffold, preferably on the exterior periphery of the middle section. Such attachment points are referred to as peripheral attachment points. In suitable embodiments, peripheral attachment points preferably coincide with points at which orthogonal fibers cross circumferential fibers.

As noted above, intervertebral discs or temporomandibular joint discs function as load transmitters and distributors to prevent high-stress bone-on-bone contact. For example an intervertebral disc comprises the annulus fibrosus and the nucleus pulposus. The nucleus pulposus is the inner gelatinous material surrounded by the annulus fibrosus. It distributes mechanical loads placed upon the disc, while the annulus fibrosus provides structural integrity and constrains the nucleus pulposus to a specific spinal region.

The annulus fibrosus has an internal structure which is very similar to the internal structure of meniscal tissue. Accordingly, torroidal concepts herein described may be utilized to construct implants for full or partial replacement of annulus fibrosus.

Figure 5A:
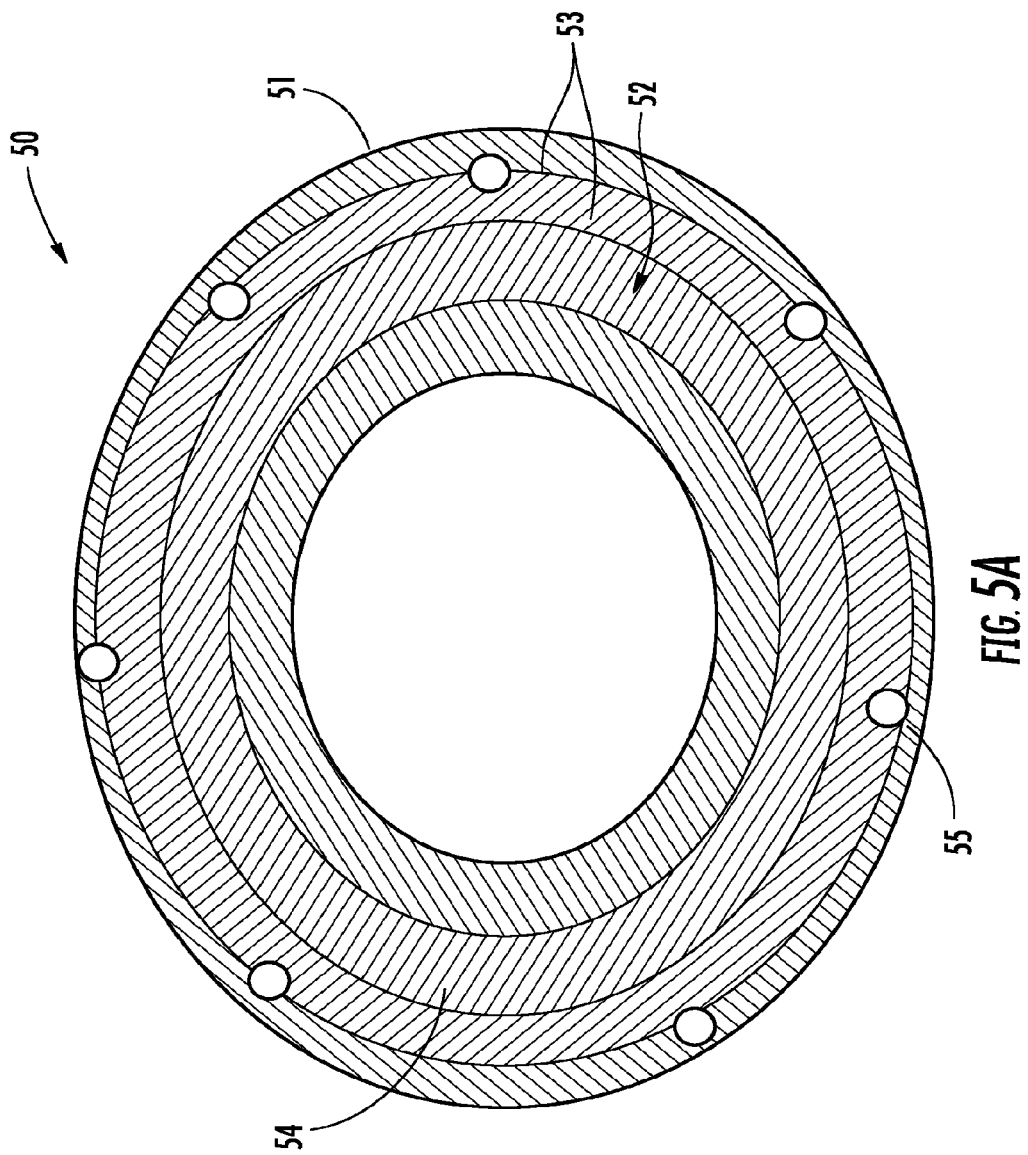
FIG. 5A is a top view of a torroidal embodiment of the instant device.
Figure 5B:
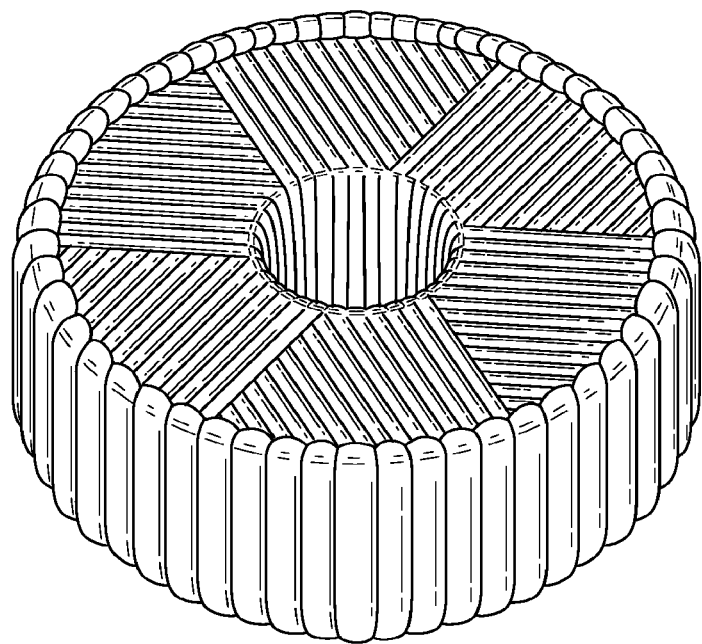
FIGS. 5B and 5C are elapsed time perspective views of a torroidal embodiment as it is being wound.
Figure 5C:
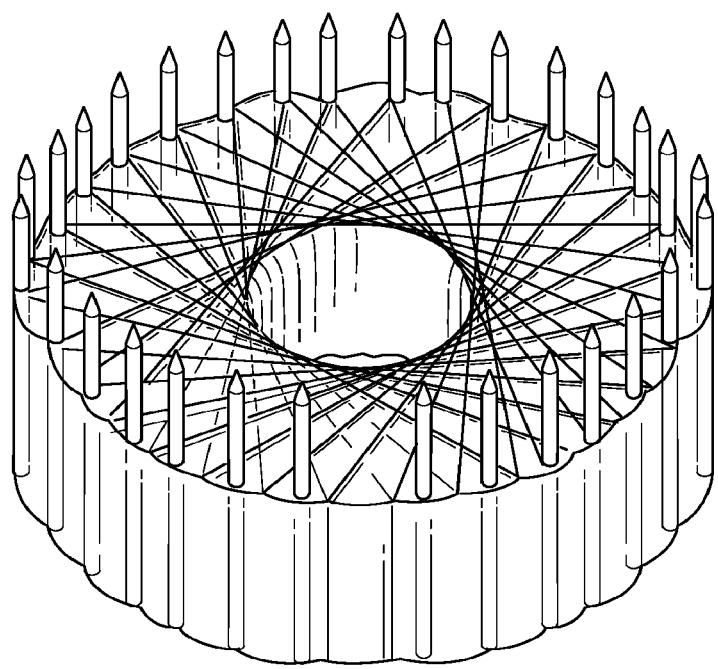

Referring to FIG. 5A, in one embodiment the instant implant 50 may comprise a torroidal-shaped scaffold 51 and a reinforcing matrix 52. The reinforcing matrix 52 may be constructed as is described above in reference to meniscus implants. In preferred embodiments, the reinforcing matrix comprises circumferential fibers 53 and orthogonal fibers 54 that cross the circumferential fibers to prevent separation of the circumferential fibers. However, in contrast to embodiments described above, the fibers forming the reinforcing matrix do not exit the scaffold and the implant may be secured by attaching the implant to the healthy tissues at peripheral attachment points 55. A device in the process of being wound is depicted in FIGS. 5B and 5C.

According to one torroidal embodiment, torroidal implants may be fabricated in the shape of a vertebral disc, wherein the torroidal-shaped scaffold defines an interior cavity filled with a biocompatible material with physical properties equivalent to the properties of the nucleus pulposus of a patient's vertebral disc. Materials suitable for use as nucleus pulposus are known and are disclosed, for example, in U.S. Pat. Nos. 5,976,186; 7,004,971 and 7,214,245, all of which are incorporated herein by reference in their entirety. Alternatively, the implant is configured to replace only the annulus fibrosus or a part of the annulus fibrosus.

For both the arcuate and torroidal constructs, both the scaffold and the reinforcing circumferential and orthogonal matrix fibers may be constructed of naturally-occurring or synthetic biocompatible materials or a combination thereof so to enable infiltration, attachment and proliferation of cells from surrounding tissues once the implant is in place. The naturally-occurring or synthetic biocompatible materials may also be bioresorbable. The scaffold and the reinforcing matrix fibers may be constructed from the same material or different materials and may be fully or partially biodegradable and may have the same or different rate of degradation.

As used herein the term "synthetic polymer" refers to polymers that are not found in nature, even if the polymers are made from naturally occurring biomaterials. The term "natural polymer" refers to polymers that are naturally occurring. The term "biocompatible" refers to materials that, in the amounts employed, do not elicit a detrimental response in the host. This term is intended to include materials that may cause some inflammation, tissue necrosis or other immune responses when introduced into the host, provided that these effects do not rise to the level of pathogenesis. The term "bioresorbable" refers to those materials that when placed in a living body at standard physiological conditions are degraded through either enzymatic, hydrolytic or other chemical reactions or cellular processes into by-products that are either integrated into or expelled from the body. It is recognized that in the literature, the terms "bioresorbable," "resorbable", "absorbable", "bioabsorbable" and "biodegradable" are frequently used interchangeably and such interchangeable meaning is intended for the present application.

Figure 6:
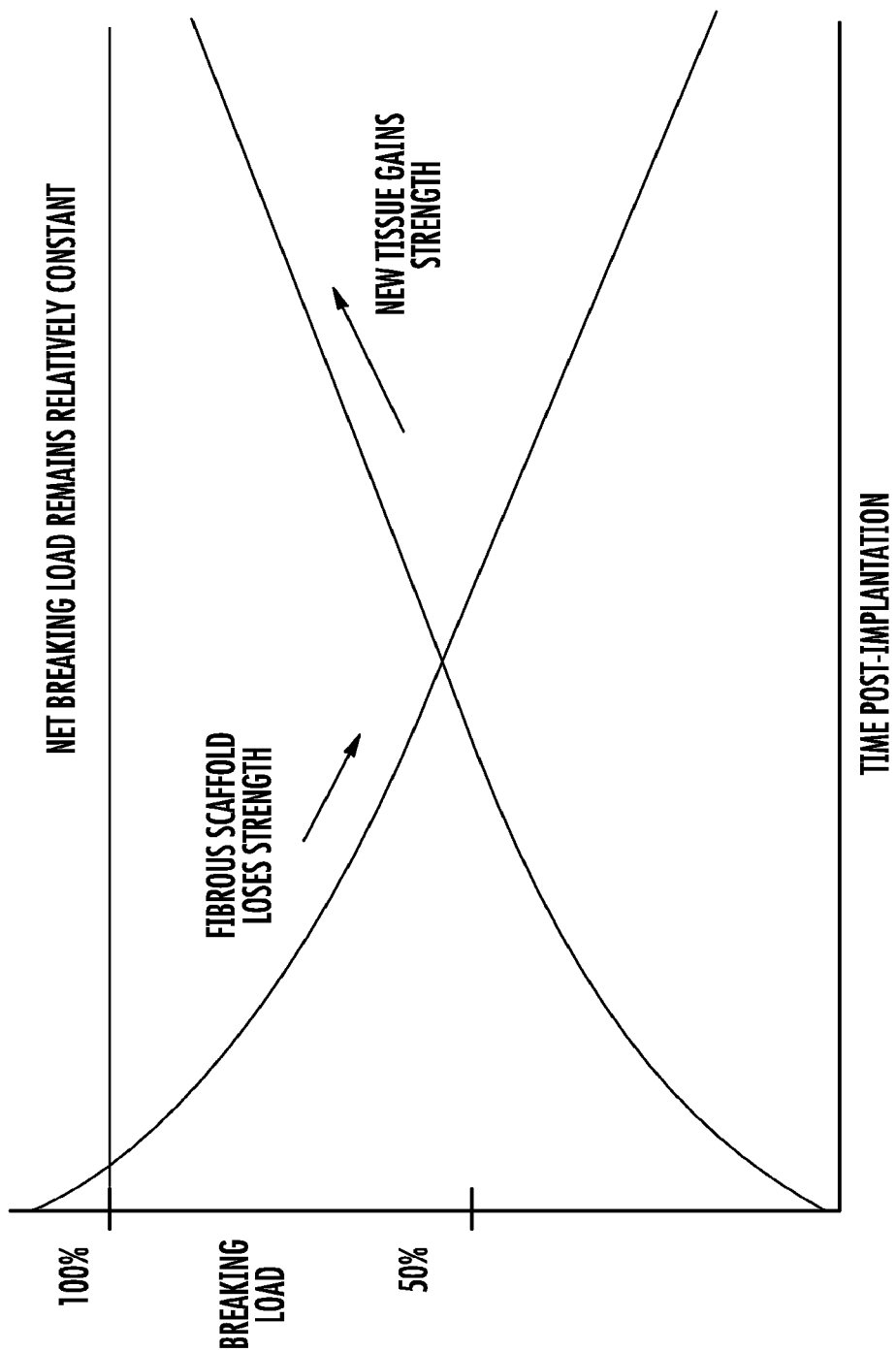
FIG. 6 presents a desirable degradation profiles for polymers suitable for use in instant devices.

In preferred embodiments, the implant is formed from biodegradable material or materials. The polymers for the instant implant are selected so the implant possesses mechanical properties which are the same or substantially similar to the mechanical properties of the native tissue being replaced. Moreover, as shown in FIG. 6, it is desirable for the mechanical properties of the implant to remain consistent as the implant is being remodeled. Accordingly, the polymers are selected so their degradation profile closely matches neo-tissue formation and remodeling, so the new tissue is afforded sufficient time to gain enough strength to compensate for the decrease in strength of the polymers. As shown in FIG. 6, this ensures that at all times the implant possesses mechanical properties resembling those of native tissue, which allows the implant to assume loads experienced in the joint at all times without failure.

Examples of suitable natural polymers include, but are not limited to, collagen, hyaluronic acid, fibrin glue, bone marrow, chitosan, alginates, celluloses, starches, silk, elastin, and other animal- or plant-derived proteins or polysaccharides. Suitable synthetic polymers include, but are not limited to, poly(alpha-hydroxy acids), poly(lactide-co-glycolide) (PLGA), poly(L-lactides) (PLLA), polylactides (PLA), polyglycolides (PGA); polyethylene, polypropylene, polyvinyl alcohol (PVA), polyethylene oxide (PEO); poly-p-dioxanone (PDO); polyarylates, polyacrylates, polycarbonates, polyesters, polycaprolactone (PCL) and combinations thereof. Suitable polyarylates and polycarbonates include, but are not limited to the tyrosine-derived polyarylates and polycarbonates disclosed by U.S. Pat. Nos. 5,099,060; 5,198,507; 5,216,115; 5,587,507; 5,658,995 and 6,048,521, the disclosures of all of which are incorporated herein by reference.

In preferred embodiments, the scaffold is an amorphous structure composed primarily of Type I collagen. In addition to collagen, other types of materials may be added to alter the scaffold's properties as necessary or desired. For example, other proteins or proteoglycans may be used, including, but not limited to, glycosaminoglycans such as chondroitin sulfate, keratan sulfate, dermatan sulfate, heparin, heparin sulfate and hyaluronic acid. The percentage of these materials in the scaffold may range between 0 and about 20% of the dry weight of the scaffold. The fiber for the reinforcing matrix may preferably be made from a bioresorbable synthetic polymer, such as a polyarylate, or a non-synthetic material, such as collagen.

The physical characteristics of the implant may be modified by using different materials for the scaffold and/or forming the reinforcing matrix from fibers of different diameter, mechanical strength, stiffness, or durability. Moreover, the physical characteristics of the implant may be modified by cross-linking the scaffold, the reinforcing matrix or both. Cross-linking may be achieved by employing a variety of known methods, including, but not limited to, chemical reaction with a carbodiimide, glutaraldehyde or formaldehyde among others; the application of energy such as radiant energy, which includes irradiation by UV light or microwave energy; dehydrothermal treatment in which water is slowly removed while the bone tissue is subjected to a vacuum; and, enzymatic treatment.

The instant implant may act as a carrier for various medical agents such as therapeutic agents and biologic factors that promote the in-growth and repair of fibrocartilage tissues and vasculature networks, and the attachment of bone tissue, where needed, including various growth factors. Suitable therapeutic agents may be selected from anti-inflammatory agents, antibiotic agents, immunosuppressive or immunomodulator agents, analgesics, anti-apoptotic agents, or combinations thereof. Small molecule therapeutics may form part of the polymer backbone of synthetic scaffold polymers, one example of which is polyaspirin, or the small molecule therapeutics may be supplied as covalent pendant polymer attachments.

The biologic factors or therapeutic agents may elute or be released from the implant as the implant degrades in the event of a bioabsorbable or a partially bioresorbable implant. Prior to elution or release by degradation, and in some embodiments that do not degrade, the biological factor or therapeutic agent is expressed on a device at the polymer surface without release. Alternatively, the implant may include additional components, such as coating or embedded bioresorbable matrices loaded with the biologic factors or therapeutic agents.

In addition, instant implants may be populated with cells of the type typically found in the type of tissue to be replaced or that can differentiate into such type of cells. By way of a non-limiting example, the instant implants may be seeded with fibroblasts, chondrocytes or mesenchymal stem cells. The mesenchymal stem cells may be derived from essentially any stem cell source, including, but not limited to bone marrow, umbilical cord blood, muscle tissue, skeletal tissue, embryonic tissue, etc. The cells may be added to the implant immediately prior to insertion of the implant into the patient's body or may be grown on the implant in the days or weeks prior to implantation. Alternatively, cells may be delivered to the implant after implantation. Techniques for preparing implants populated with cells are known in the art and are disclosed for example in U.S. Pat. No. 6,103,255, the disclosure of which are incorporated herein by reference.

Moreover, the instant implant may include radio-opaque, echogenic materials and magnetic resonance imaging (MRI) responsive materials (i.e., MRI contrast agents) to aid in visualization of the implant under ultrasound, fluoroscopy and/or MRI. For example, a device may be made with or coated with a composition which is echogenic or radiopaque (e.g., made with echogenic or radiopaque with materials) or, by the addition of microspheres or bubbles which present an acoustic interface). For visualization under MRI, contrast agents may be incorporated into or onto the implant. In some embodiments, the instant implant may include radio-opaque or MRI visible markers.

The instant implants may, alternatively, or in addition, be visualized under visible light, using fluorescence, or by other spectroscopic means. Visualization agents that can be included for this purpose include dyes, pigments, and other colored agents. In one aspect, the instant implant may further include a colorant to improve visualization of the implant in vivo and/or ex vivo. Frequently, implants can be difficult to visualize upon insertion, especially at the margins of implant. A coloring agent can be incorporated into the instant implant to reduce or eliminate the incidence or severity of this problem. The coloring agent provides a unique color, increased contrast, or unique fluorescence characteristics to the implant so it is readily visible (under visible light or using a fluorescence technique) and easily differentiated from its implant site.

In another aspect, a method for implantation of the instant implant in place of a damaged tissue is provided. The instant devices may be implanted by surgical or arthroscopic techniques. In general, to implant the instant device the tissue in need of replacement is removed, the implant is inserted to replace the removed tissue and is fixed in place to tissue adjacent the implantation site, for example, by suturing. When a compressive force is applied to the instant implant after implantation, the force is converted into tensile loads along circumferential fibers in the reinforcing matrix.

By way of non-limiting example, the instant implant is particularly useful for treatment of anatomical variances in meniscus, such as tears or discoid meniscus. The instant implant may be used in partial, sub-total, or total meniscectomy. The damaged meniscal tissue, representing a total or part of a meniscus, is removed and the instant implant, tailored to have the same size and shape as the removed tissue, is placed in its place.

In total or subtotal meniscectomy, the implant is secured in place by attaching the anterior and posterior attachment points of the implant to the tibial plateau. One or more holes may be drilled in the tibial plateau, preferably, at the site of the anterior and posterior attachments of the original meniscus. The anterior and posterior attachment points may be inserted into these holes and secured in place by any known techniques, such as using metal or polymeric interference screws, pressure fitting, stapling, suturing, and so forth. Such tibial attachments enable generation of hoop stresses in the implant.

In addition, the implant may be further secured in place by suturing it to healthy tissue adjacent to the implantation site, namely the joint capsule, cartilage, or remaining meniscal tissue, at one or more peripheral attachment points in the middle section of the scaffold. In a partial meniscectomy, the meniscus may be secured in place exclusively at one or more peripheral attachment points in addition to being sutured to the remaining meniscus tissue.

In yet another aspect, a method for fabrication of the instant device is provided. First, the reinforcing matrix is formed from one or more fibers, preferably in a shape of the soft tissue the implant is designed to replace. The matrix may be formed by any method known and used in the art for physically interlacing fibers, such as, without limitation, weaving, braiding, knitting, or combination thereof. Alternatively, the fibers may be attached using chemical means such as gluing or cross-linking the fibers together. Moreover, a polymer may be molded into the shape of a three-dimensional matrix.

Second, the reinforcing matrix is inserted into a mold assembly or a mold assembly is formed around the matrix. The mold preferably has the same shape as the soft tissue in need of replacement. In some embodiments, the ends of the fiber forming the reinforcing matrix extend outside each end of the mold assembly to form the attachment points. Third the polymer is injected into the mold assembly to form the scaffold body, which is then solidified.

The process for solidifying the scaffold depends on the polymer used to form the scaffold. For example, if collagen is used, the implant assembly may be lyophilized. In some embodiments, the implant may be cross-linked to alter its physical characteristics. Moreover, additives such as cells, growth factors, medical agents, and/or labels, etc., may be added to the implant at any point during the fabrication of the device according to standard techniques known and used in the field.

As noted above, in some embodiments both the fiber network matrix and the scaffold have same the shape and geometry as the soft tissue they are made to replace. For example, in embodiments for the knee, the reinforcing matrix and the mold assembly may be constructed as a c-shaped disc with a wedge-like cross-section, similar to a knee meniscus.

EXAMPLES

Example I

Fabrication of Meniscus Implant

The mold for the scaffold was made up of a plastic base plate, outer glass tube, inner sphere, and 24 clothing pins. Twenty-four holes (0.05 mm) were drilled through the large face of the plate as shown in FIG. 7A. Twenty-two holes were at equal intervals forming a semi-circle with the remaining two holes opposite the center of the semi-circle.

Figure 7B:
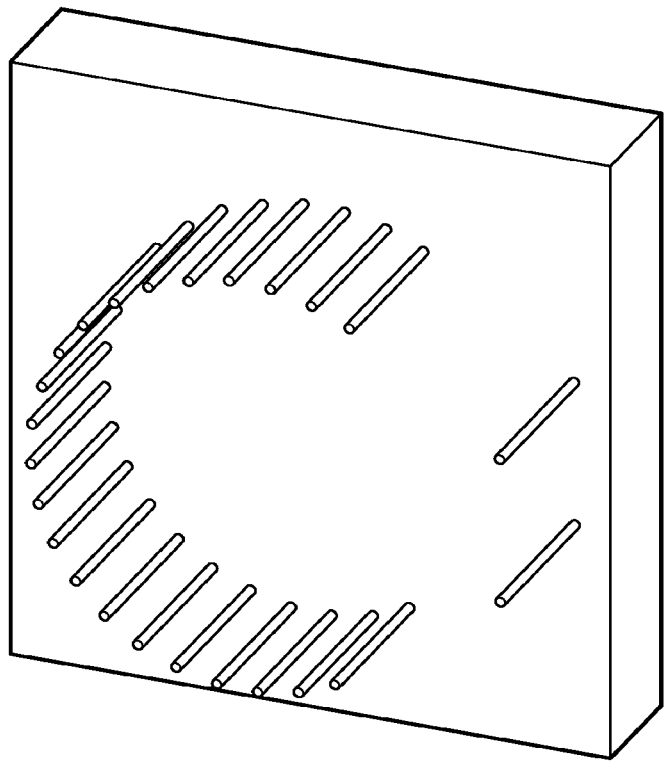
FIGS. 7A-7B show a base plate pattern for fabrication of meniscus scaffolds.
Figure 7A:
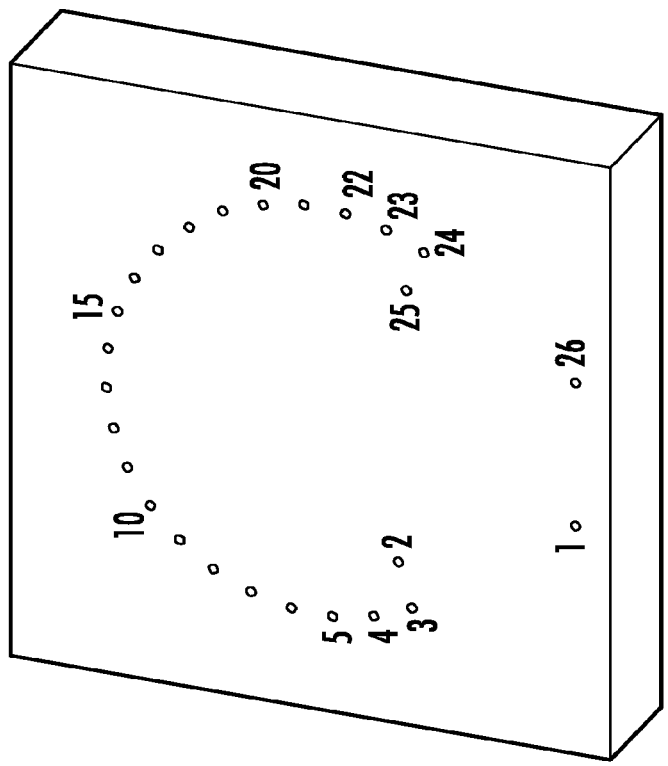

Twenty-four pins were pushed through the holes forming the pattern shown in FIG. 7B. For purposes of explanation, each hole of the base plate was assigned a number from 1 through 26. Holes 2 through 25 define the actual dimensions of the meniscus scaffold, while holes 1 and 26 define the anchor points for the scaffold.

Referring to FIG. 8(a)-8(g), a continuous length of polymer fiber was wrapped around the pins in a quasi-circumferential pattern. Starting from point 1, fibers were wrapped and pivoted at one of six different off-tangent angles from the pins: (FIG. 8(a)) 11.25°, (FIG. 8(b)) 28.125°, (FIG. 8(c)) 39.375°, (FIG. 8(d)) 50.625°, (FIG. 8(e)) 61.875°, and (FIG. 8(f)) 73.125°. This continued until point 26, at which time the fiber was wrapped in reverse. For pins 2 through 5 and 22 through 25, fibers were wrapped back to point 1 or 26 for formation of anchor bundles. This process was repeated for each angle to produce a complete pattern shown in FIG. 8(g) and to form a plurality of nodes at each pin 2 to 25, each node being a point from which a plurality of bioresorbable orthogonal fibers diverge at at least two different angles. Depending on the amount of fiber desired for reinforcing, this pattern was repeated several times.

The pin pattern allows for a semi-lunar shape to be formed along with two bundles of fibers at each horn for formation of the anchor plugs. After wrapping was complete, the fibers were teased up to form a wedge shape (cross-section). The fiber wrapped assembly was then stored in a low humidity chamber until the collagen dispersion was ready for the molding step.

A collagen dispersion was made by swelling lyophilized type I bovine collagen in an acid solution (pH≈2.4). The appropriate amount of collagen was added to a volume of acid (e.g. for 1% dispersion, 1.0 g collagen added to 100 ml acid). As noted above, in different embodiments, other materials may be added to alter the properties of the matrix portion and dispersion concentrations may be modified. The collagen/acid mixture was then homogenized using a high speed blender (pulse blending to reduce possible heat denaturation effects on collagen). After about five minutes of pulse blending (mix≈5 seconds, wait for ≈1 minute), the mixture was de-aerated under vacuum for about five minutes. About 8 ml of the dispersion was drawn up into a syringe using a 20 gauge needle to prevent large, non-homogenized chunks of collagen from entering scaffold.

The outer glass tube and inner sphere were placed in position around the base plate to complete the mold assembly. The collagen dispersion was injected into the mold, ensuring no air bubbles were introduced into the scaffold body. The assembly was wrapped in a thin plastic bag and submerged in an ethanol-dry ice bath (.about.−30° C.) for about 10 minutes. The resultant solid was then transferred to a standard freezer for about an hour to ensure complete freezing. After the entire assembly was frozen completely, it was lyophilized.

After lyophilization, the pins were pulled from the base plate, resulting in a fiber reinforced collagen sponge with a semi-lunar shape, a wedge-shaped cross-section, a series of small holes around its periphery and a plurality of nodes at the circumference of the sponge. The extra lengths of fibers from the ends of the scaffold were used to form anchor plugs which can be implanted into the tibial plateau. A medical grade polyurethane adhesive was used to form the plugs. The ends of the fiber bundles were dipped in the adhesive and formed to into a bullet-shaped plug.

After construction, the scaffolds were crosslinked to increase the durability of the collagen matrix. The implant was stored dry until use.

Example 2

Mechanical Evaluation

Figure 9:
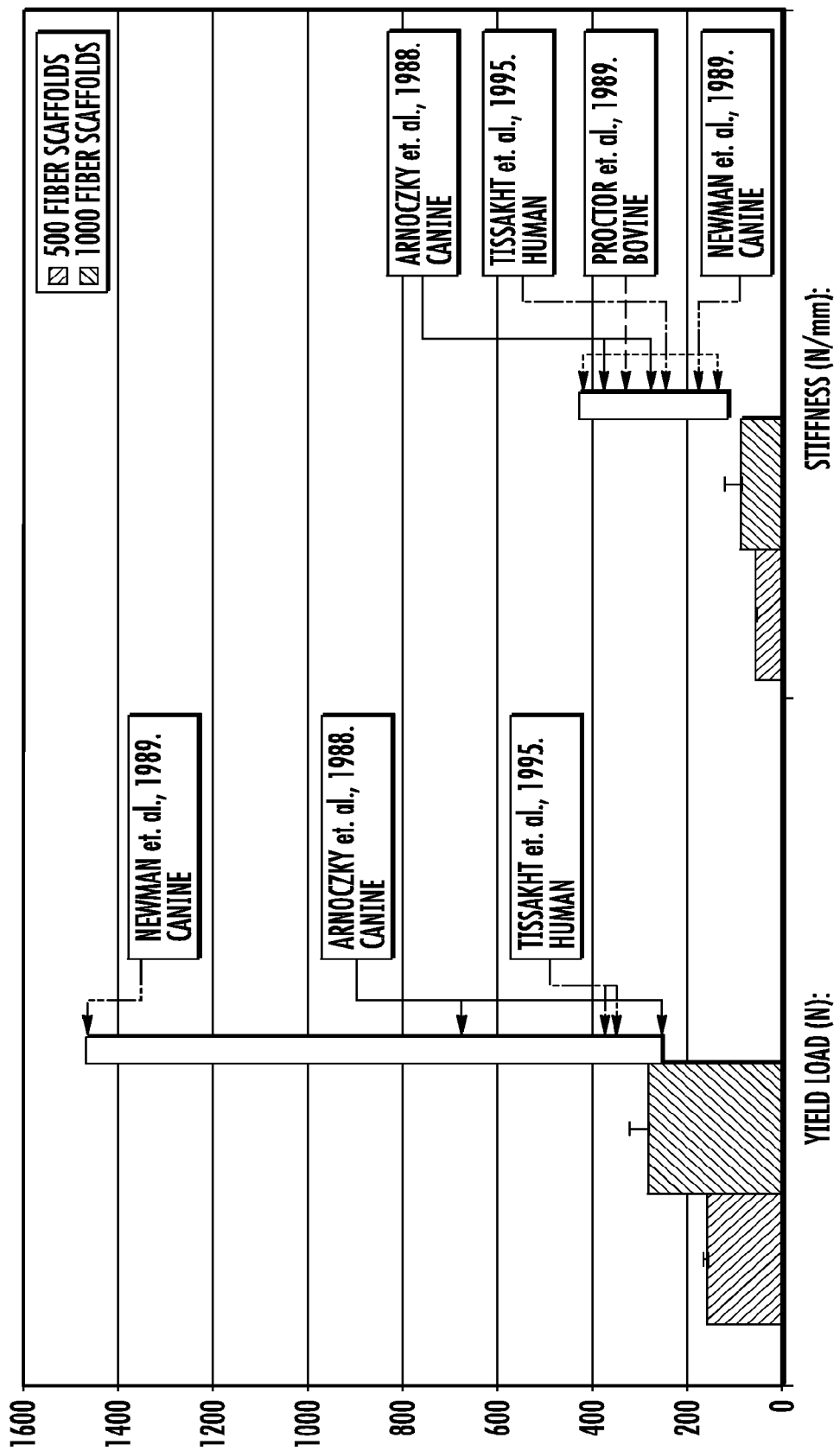
FIG. 9 presents the results from a primary mechanical evaluation of the tensile strength of the scaffold of the invention.

A preliminary mechanical evaluation was carried out using standard tensile testing. The following four groups were tests: no scaffold, collagen scaffold without reinforcement ("100 Coll. Scaffold), collagen scaffold with a reinforcing fibers consisting of 500 fibers ("500 Fiber Scaffold"), and collagen scaffold with a reinforcing fibers consisting of 1000 fibers ("1000 Fiber Scaffold). In this evaluation the anterior and posterior fiber ends were soaked in poly-urethane glue and dried overnight. They were then loaded into an Instron Mechanical Tester (model 4202) and pulled in tension until failure at a speed of 10 mm/min. The structural properties were calculated from recorded data. The results are set forth in FIG. 9.

An advanced mechanical evaluation of the meniscus replacement of the invention measured pressure distribution on the tibial plateau but did not measure circumferential hoop stresses developed from axial compressive loads using "indirect" measurement. The results are shown in FIGS. 10A-13B. With regard to the contact area, no significant difference was seen between the "No Scaffold" and "100% Coll. Scaffold" groups while there were significant differences between "No Scaffold" and "100% Coll. Scaffold" groups and "500 Fiber Scaffold" and "1000 Fiber Scaffold" groups.

Example 3

Biological Evaluation

The scaffold was evaluated by characterizing the in vitro biological response to the scaffold as well as preliminary in vivo evaluations in rabbit models.

Figure 14B:
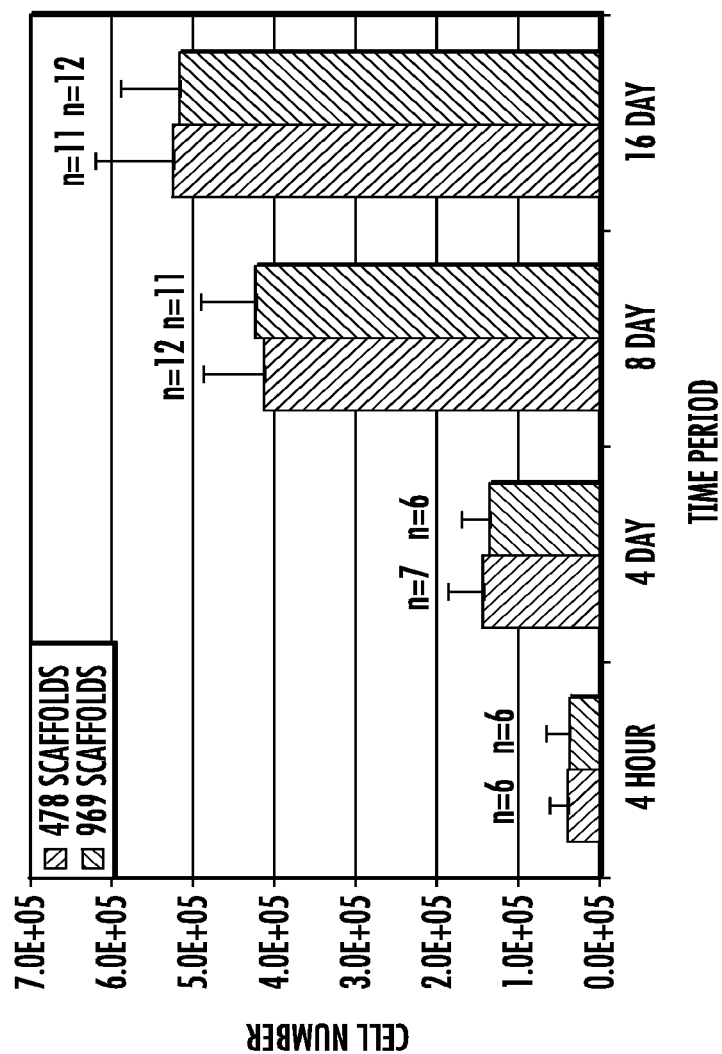
FIGS. 14A-14B present the results of an in vitro evaluation of the scaffold of the invention.
Figure 14A:
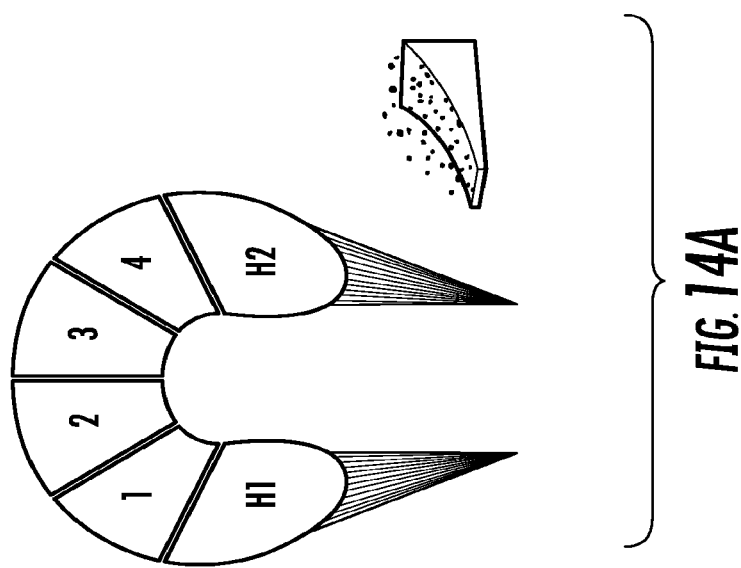
Figure 15A:
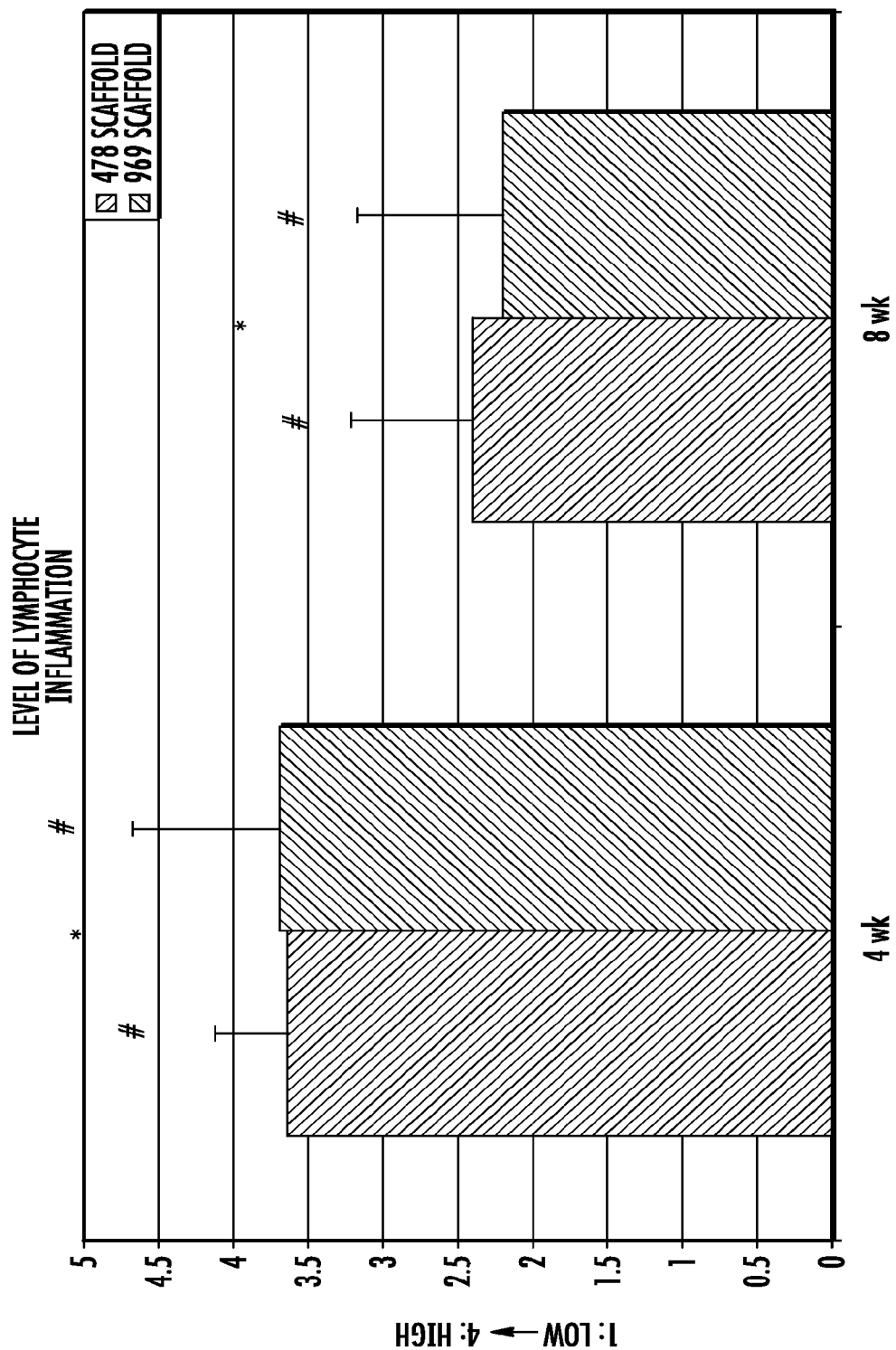
FIGS. 15A-15F present the results of an in vivo evaluation of the scaffold of the invention.
Figure 15B:
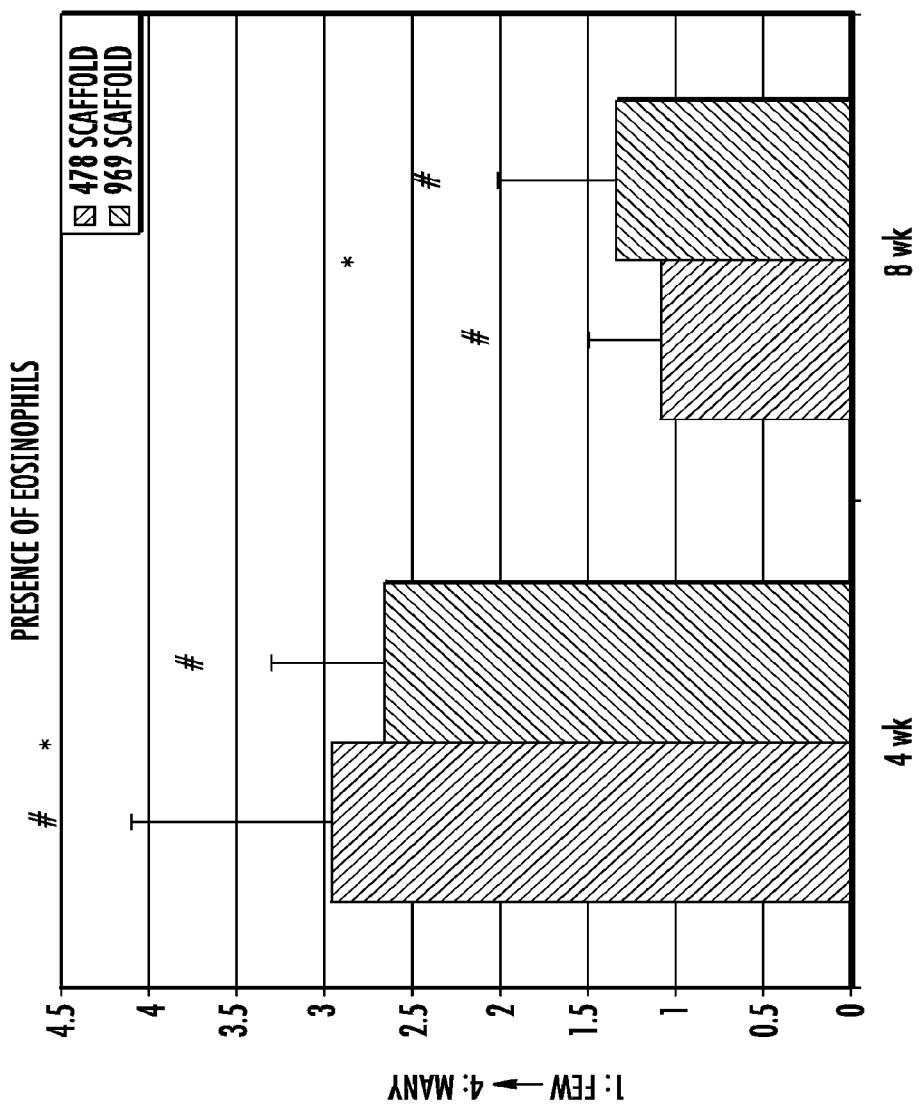
Figure 15C:
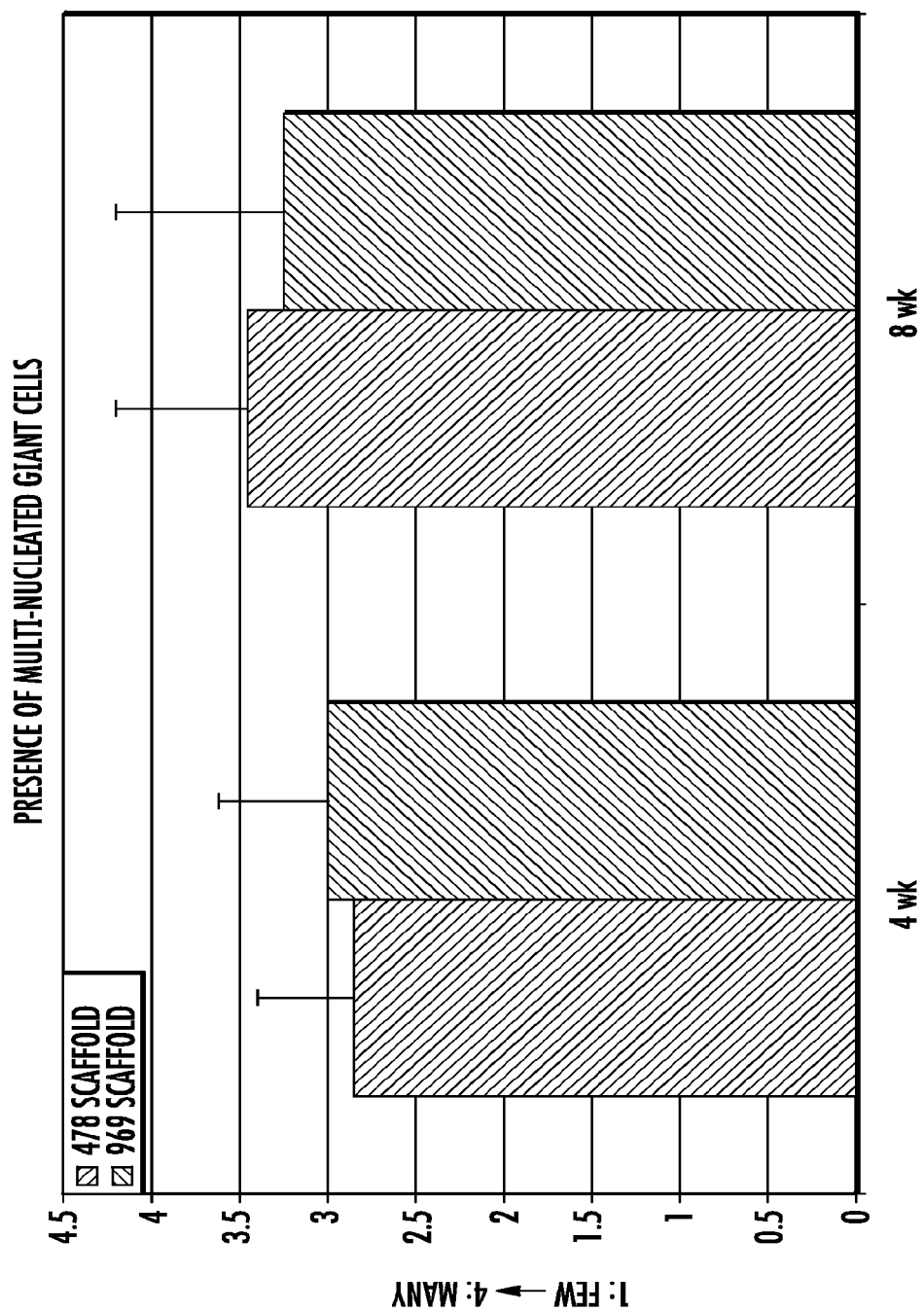
Figure 15D:
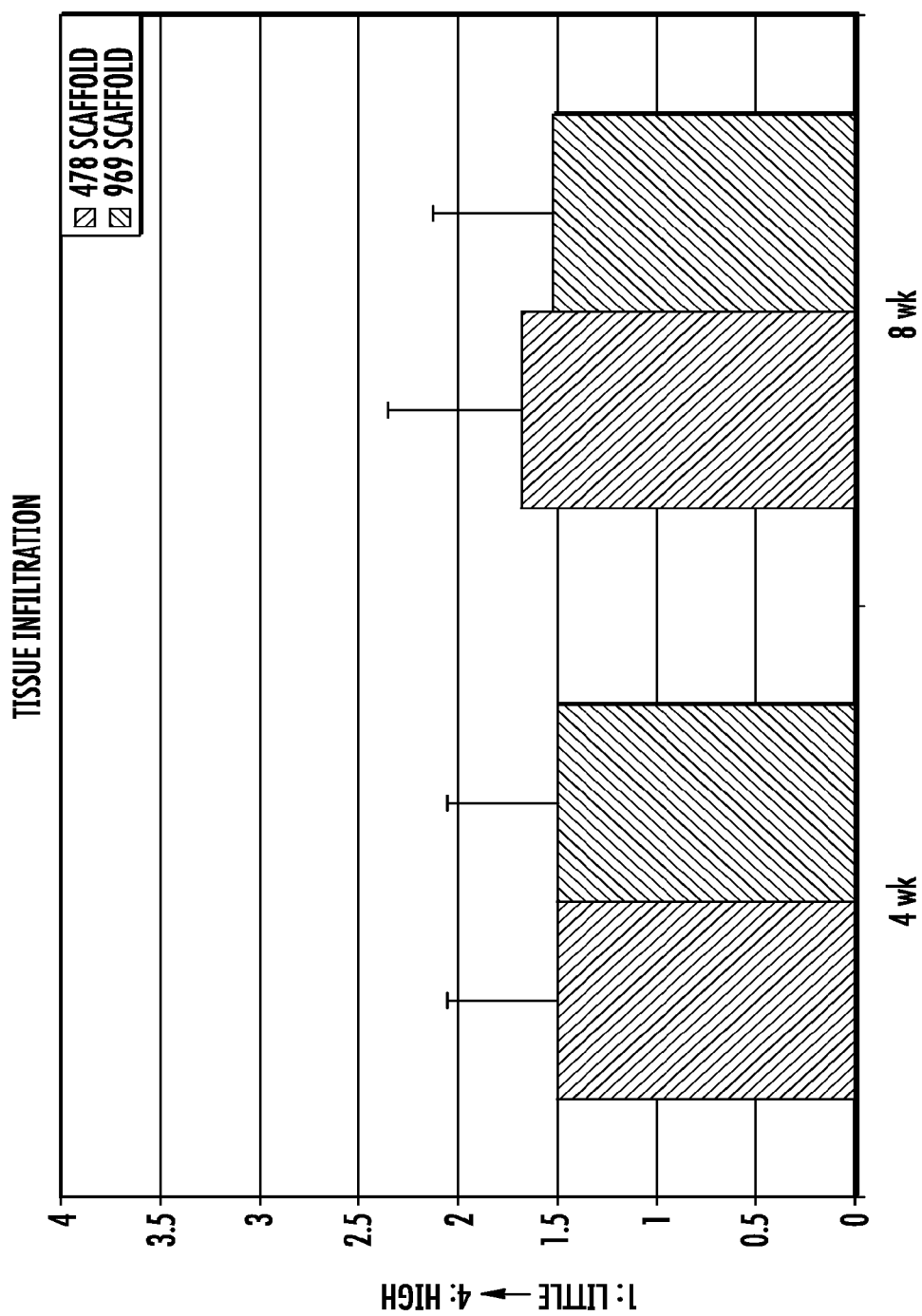
Figure 15E:
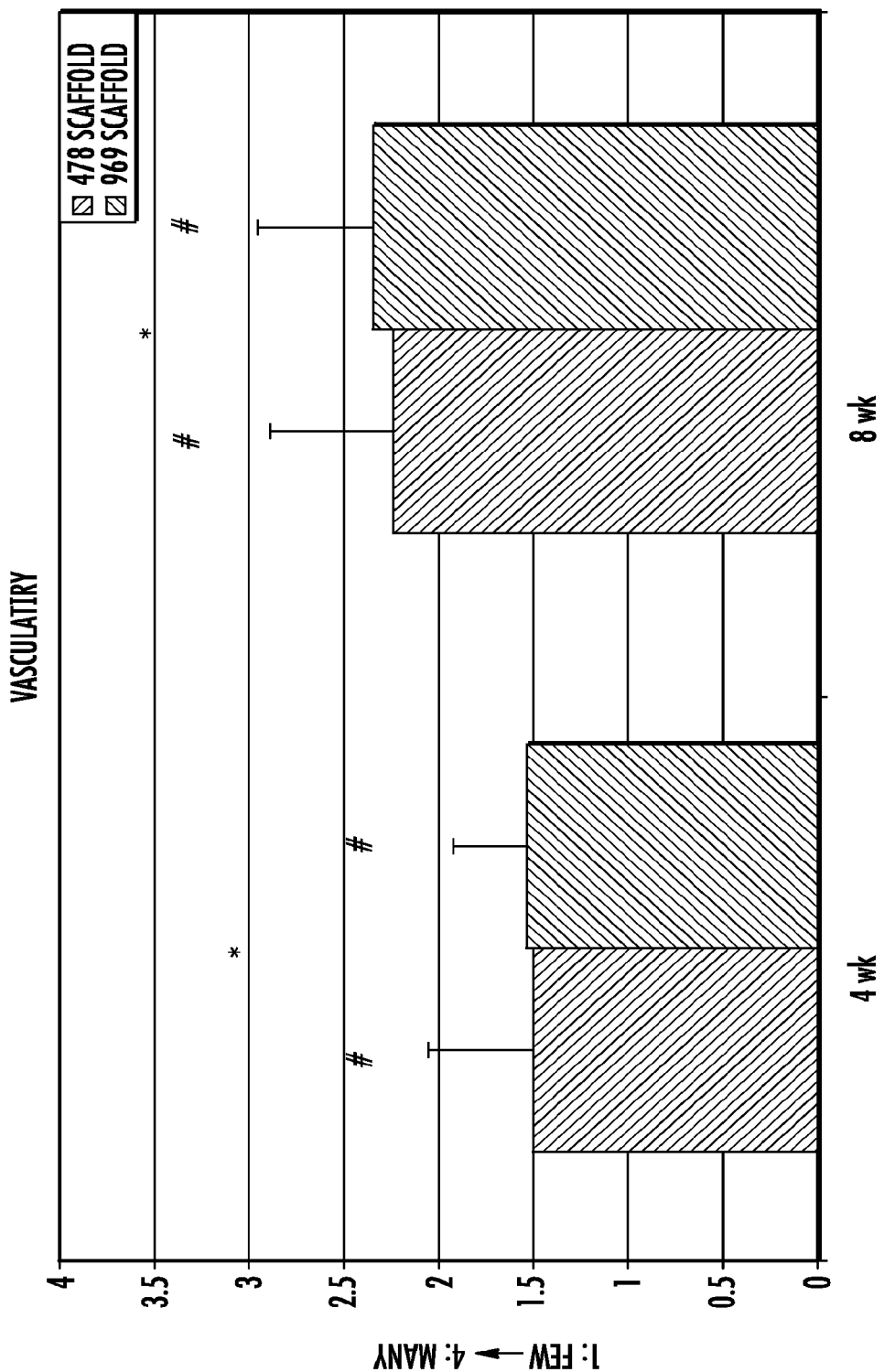
Figure 15F:
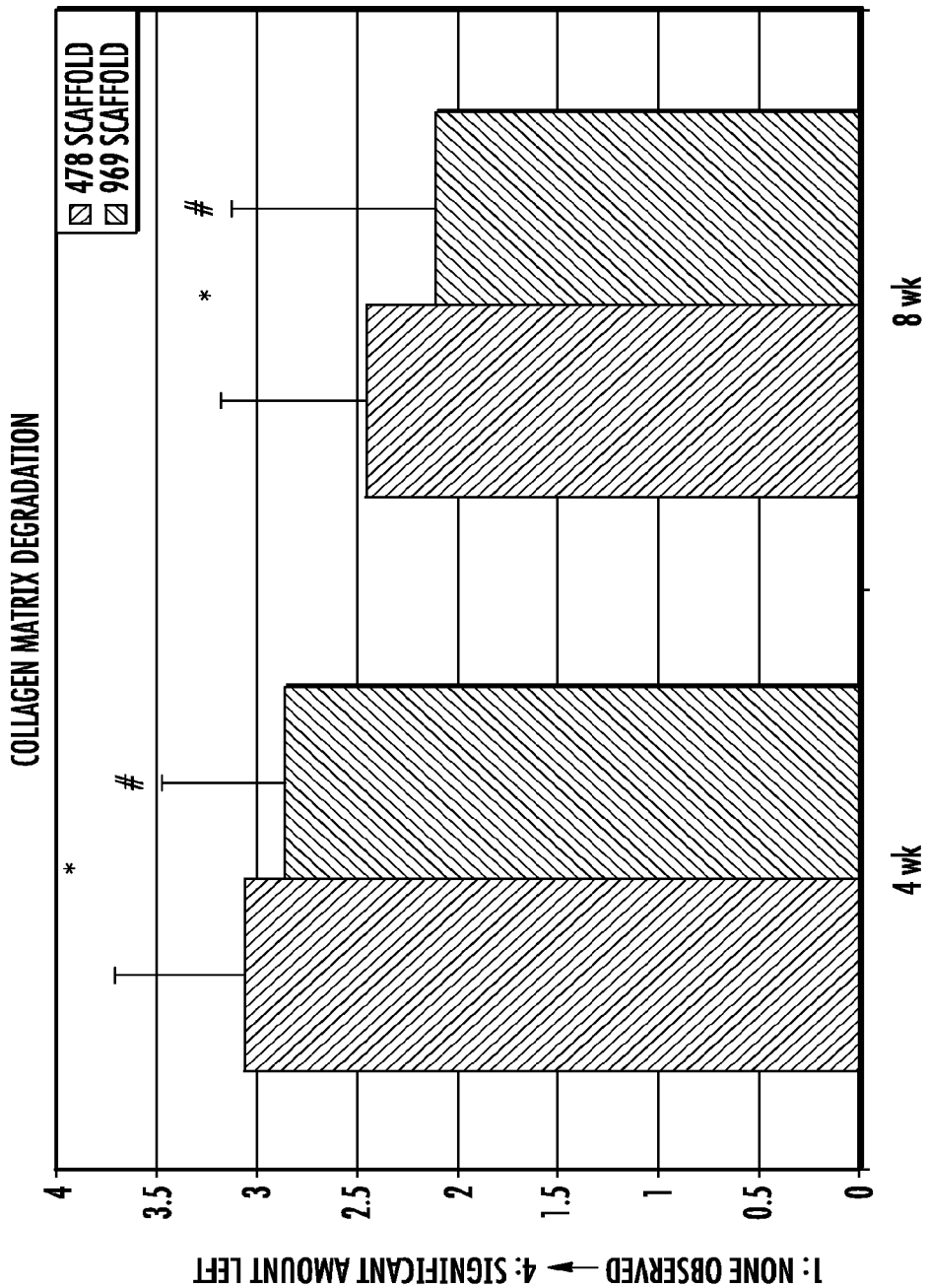

In an in vitro evaluation a fibrochondrocyte cell line was harvested from NZW rabbits and cultured until $2^{nd}/3^{rd}$ passage. Scaffolds were sectioned into 6 wedges as shown in FIG. 14A. $1 \times 10^5$ cells were seeded onto the anterior surface of each section and the cell-seeded scaffolds were incubated in complete cell media for 4 hrs, 4 days, 8 days, or 16 days. The scaffolds were then analyzed with either MTS assay or standard H&E histology. A normal growth curve was observed with a significant difference between all time points, as seen in FIG. 14B. There was no significant difference between the two scaffold types of the invention.

In a non-functional in vivo evaluation in rabbits, two sections were cut from each scaffold for 4 and 8 week time points. Two scaffold designs were studied (500 fiber and 1,000 fiber scaffolds). A medial parapatellar arthrotomy created a pocket for an implant between medial joint capsule and medial femoral condoyle and the scaffold was inserted. The scaffold therefore was exposed to harsh synovial environments but was under no significant load and did not interfere with joint function. Both knees of each rabbit were used with the 500 fiber scaffold on one side and the 1000 fiber scaffold in the other. At sacrifice the scaffolds were excised along with 2-3 mm of surrounding tissue. The samples were preserved in buffered formalin and then processed histologically with H&E stain. The results are shown in FIGS. 15A-15F.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A method for fabricating a fibrocartilage implant having a circumference, a length, a width, and a height, the method comprising:
    forming a reinforcement matrix defined by a network of bioresorbable circumferential fibers and a network of bioresorbable orthogonal fibers, the reinforcement matrix having a three-dimensional shape and geometry which are substantially the same as a three-dimensional shape and geometry of the fibrocartilage implant; and
    embedding the reinforcement matrix within a bioresorbable scaffold;
    wherein the step of forming the reinforcement matrix includes:
        arranging at least one fiber circumferentially and orthogonally in crisscrossed patterns at different levels along the height of the implant such that the bioresorbable circumferential fibers are positioned essentially parallel to the circumference of the fibrocartilage implant and the bioresorbable orthogonal fibers cross the bioresorbable circumferential fibers at various angles, including acute angles,
        wherein the arranging comprises extending the at least one fiber from each one of a plurality of nodes at the circumference of the fibrocartilage implant, each node being a point from which plurality of bioresorbable orthogonal fibers diverge at at least two different angles in length-width planes of the implant, wherein each bioresorbable orthogonal fiber extends in a substantially straight path from one node to at least one other different node; and
    wherein the reinforcement matrix translates an axial compressive force on the bioresorbable scaffold to tensile loads along the network of bioresorbable circumferential fibers.

2. The method of claim 1, wherein the bioresorbable orthogonal fiber network is configured to prevent separation of the bioresorbable circumferential fiber network.

3. The method of claim 1, wherein the bioresorbable scaffold defines a curved path between anterior and posterior ends.

4. The method of claim 3, wherein the bioresorbable circumferential fiber network extends between the anterior and posterior ends along the curved path and exits the anterior and posterior ends of the scaffold to form respective anterior and posterior attachment points.

5. The method of claim 4, further comprising defining at least one peripheral attachment point between the anterior and posterior ends.

6. The method of claim 5, wherein the at least one peripheral attachment point coincides with a point at which a bioresorbable circumferential fiber of the bioresorbable circumferential fiber network intersects a bioresorbable orthogonal fiber of the bioresorbable orthogonal fiber network.

7. The method of claim 1, wherein the bioresorbable scaffold is formed from a material selected from the group consisting of proteins, proteoglycans, biocompatible synthetic polymers and combinations thereof.

8. The method of claim 7, wherein the proteins comprise collagen.

9. The method of claim 8, wherein the collagen is cross-linked.

10. The method of claim 1, wherein at least one of the bioresorbable scaffold, the bioresorbable circumferential fiber network, or the bioresorbable orthogonal fiber network comprises a biocompatible synthetic polymeric material.

11. The method of claim 1, wherein the three-dimensional shape and geometry of the reinforcement matrix is an arcuate c-shape wedge or a torroidal-shape structure.

12. The method of claim 11, wherein the implant is fabricated in a shape of a knee meniscus.

13. The method of claim 11, wherein the implant is fabricated in a shape of a vertebral disc or an articular disc for a joint.

14. The method of claim 13, wherein the implant is in the shape of a vertebral disc and the scaffold has a torroidal-shape which defines an interior cavity filled with a biocompatible material with physical properties equivalent to properties of a nucleus pulposus of a human vertebral disc.

15. The method of claim 13, wherein the implant is in a shape of an articular disc for a temporomandibular joint or a wrist.

16. The method of claim 1, wherein the reinforcement matrix is formed of a simile, continuous fiber.

17. The method of claim 1, wherein the bioresorbable circumferential and orthogonal fibers are formed by same or different strands of fiber or a combination thereof.

* * * * *